US011833141B2

(12) United States Patent
Kandula

(10) Patent No.: US 11,833,141 B2
(45) Date of Patent: Dec. 5, 2023

(54) TOPICAL FORMULATIONS AND COMPOSITIONS

(71) Applicant: AVACA PHARMA PRIVATE LIMITED, Medak (IN)

(72) Inventor: Mahesh Kandula, Andhra Pradesh (IN)

(73) Assignee: Avaca Pharma Private Limited, Medak (IN)

( * ) Notice: Subject to any disclaimer, the term of this patent is extended or adjusted under 35 U.S.C. 154(b) by 0 days.

(21) Appl. No.: 17/942,015

(22) Filed: Sep. 9, 2022

(65) Prior Publication Data

US 2023/0020927 A1 Jan. 19, 2023

Related U.S. Application Data

(63) Continuation of application No. PCT/IB2022/051367, filed on Feb. 16, 2022.

(30) Foreign Application Priority Data

Feb. 17, 2021 (IN) ............................. 202141006680
Apr. 8, 2021 (IN) ............................. 202141016620
Oct. 24, 2021 (IN) ............................. 202141048441
Nov. 13, 2021 (IN) ............................. 202141052147

(51) Int. Cl.
*A61K 31/445* (2006.01)
*A61K 31/135* (2006.01)
*A61K 31/47* (2006.01)
*A61K 9/00* (2006.01)

(52) U.S. Cl.
CPC .......... *A61K 31/445* (2013.01); *A61K 9/0014* (2013.01)

(58) Field of Classification Search
CPC ..... A61K 31/445; A61K 31/135; A61K 31/47
USPC ........................................ 514/311, 317, 648
See application file for complete search history.

(56) References Cited

U.S. PATENT DOCUMENTS

| 8,173,812 | B2 * | 5/2012 | Montana | ................. | A61P 11/02 |
| | | | | | 546/159 |
| 8,389,515 | B2 * | 3/2013 | Singh | ...................... | A61P 21/04 |
| | | | | | 544/73 |
| 11,155,557 | B2 * | 10/2021 | Romero | ............... | C07D 519/00 |

FOREIGN PATENT DOCUMENTS

| CN | 1813743 | A | 8/2006 |
| CN | 1957941 | A | 5/2007 |
| IN | 79/DEL/2003 | A | 6/2009 |
| IN | 2886/DEL/2005 | A | 10/2009 |
| IN | 2039/DEL/2009 | A | 4/2011 |
| IN | 689/CHE/2009 | A | 2/2012 |
| IN | 2620/CHE/2013 | A | 3/2015 |
| IN | 351665 | B | 11/2020 |
| WO | 2006131737 | A2 | 12/2006 |
| WO | 2007070517 | A2 | 7/2007 |
| WO | 2011067667 | A2 | 6/2011 |
| WO | 2011151733 | A2 | 12/2011 |
| WO | 2015107544 | A2 | 7/2015 |
| WO | 2020194308 | A1 | 10/2020 |
| WO | 2021035086 | A1 | 2/2021 |
| WO | 2021083989 | A1 | 5/2021 |
| WO | 2021216915 | A1 | 10/2021 |

OTHER PUBLICATIONS

Matterne U, Böhmer MM, Weisshaar E, Jupiter A, Carter B, Apfelbacher CJ. Oral H1 antihistamines as 'add-on' therapy to topical treatment for eczema. Cochrane Database Syst Rev. Jan. 22, 2019;1(1):CD012167. doi: 10.1002/14651858.CD012167.pub2. PMID: 30666626; PMCID: PMC6360926.

Iriarte Sotés P, Armisén M, Usero-Bárcena T, Rodriguez Fernández A, Otero Rivas MM, Gonzalez MT, Meijide Calderón A, Veleiro B; Urtigal, the Galician Group of Interest in Urticaria. Efficacy and Safety of Up-dosing Antihistamines in Chronic Spontaneous Urticaria: A Systematic Review of the Literature. J Investig Allergol Clin Immunol. Jul. 26, 2021;31(4):282-291. doi: 10.18176/jiaci.0649. Epub Oct. 8, 2020. PMID: 33030434.

Zhao X, Liu R, Chen Y, Hettinghouse A, Liu C. Cytosolic Phospholipase A2 Is Required for Fexofenadine's Therapeutic Effects against Inflammatory Bowel Disease in Mice. Int J Mol Sci. Oct. 15, 2021;22(20):11155. doi: 10.3390/ijms222011155. PMID: 34681815; PMCID: PMC8539349.

Shimizu H, Ito A, Sakurada K, Nakamura J, Tanaka K, Komatsu M, Takeda M, Saito K, Endo Y, Kozaki T, Shoda M, Kuriyama H. AK106-001616, a Potent and Selective Inhibitor of Cytosolic Phospholipase A2: In Vivo Efficacy for Inflammation, Neuropathic Pain, and Pulmonary Fibrosis. J Pharmacol Exp Ther. Jun. 2019;369(3):511-522. doi: 10.1124/jpet.118.255034. Epub Apr. 10, 2019. PMID: 30971478.

Liu R, Chen Y, Fu W, Wang S, Cui Y, Zhao X, Lei ZN, Hettinghouse A, Liu J, Wang C, Zhang C, Bi Y, Xiao G, Chen ZS, Liu CJ. Fexofenadine inhibits TNF signaling through targeting to cytosolic phospholipase A2 and is therapeutic against inflammatory arthritis. Ann Rheum Dis. Nov. 2019; 78(11):1524-1535. doi: 10.1136/annrheumdis-2019-215543. Epub Jul. 13, 2019. PMID: 31302596; PMCID: PMC8157820.

Ashenager MS, Grgela T, Aragane Y, Kawada A. Inhibition of cytokine-induced expression of T-cell cytokines by antihistamines. J Investig Allergol Clin Immunol. 2007; 17(1):20-6. PMID: 17323859.

(Continued)

*Primary Examiner* — Raymond J Henley, III
(74) *Attorney, Agent, or Firm* — S. Elizabeth Miller, Esq.

(57) ABSTRACT

The present disclosure provides a pharmaceutical composition comprising H1 antagonist or a salt or a hydrate or a solvate thereof: a diluent; a solvent; an emollient; a humectant; a preservative; an emulsifier; and a surfactant, said composition being formulated as a topical formulation. The composition may include one or more additional active agents. The composition is formulated into a topical lotion, solution, spray, emulsion, emulsion of water and oil (oil in water or water in oil emulsion), gel, or cream. The compositions of the present disclosure may find utility in treatment of allergic conditions/diseases of skin. It further relates to a method of treating an allergic condition using the compositions of the present disclosure.

17 Claims, 3 Drawing Sheets

(56) References Cited

OTHER PUBLICATIONS

Ningombam A, Handa S, Srivastava N, Mahajan R, De D. Addition of oral fexofenadine to topical therapy leads to a significantly greater reduction in the serum interleukin-31 levels in mild to moderate paediatric atopic dermatitis. Clin Exp Dermatol. Apr. 2022;47(4):724-729. doi: 10.1111/ced.15032. Epub Jan. 6, 2022. PMID: 34826148.
Seong-Joon Koh, Ji Won Kim, Byeong Gwan Kim, Kook Lae Lee, Jaeyoung Chun and Joo Sung Kim. Effects of Fexofenadine in Intestinal Inflammation. Journal of Pharmacology and Experimental Therapeutics Mar. 1, 2015, 352 (3) 455-461; DOI: https://doi.org/10.1124/jpet.114.217844.
Kordulewska NK, Kostyra E, Cieślińska A, Fiedorowicz E, Jarmołowska B. Cytokine production by PBMC and serum from allergic and non-allergic subjects following in vitro histamine stimulation to test fexofenadine and osthole anti-allergic properties. Eur J Pharmacol. Nov. 15, 2016;791:763-772. doi: 10.1016/j.ejphar.2016.10.020. Epub Oct. 15, 2016. PMID: 27756601.
Joanna Marciniak, Adam Reich And Jacek C. Szepietowski, Quality of Life of Parents of Children with Atopic Dermatitis, Acta Derm Venereol 2017; 97: 711-714.
Anderson P, Austin J, Lofland JH, Piercy J, Joish VN. Inadequate Disease Control, Treatment Dissatisfaction, and Quality-of-Life Impairments Among US Patients Receiving Topical Therapy for Atopic Dermatitis. Dermatol Ther (Heidelb). Oct. 2021;11(5):1571-1585. doi: 10.1007/s13555-021-00580-2. Epub Jul. 15, 2021. PMID: 34268709; PMCID: PMC8484432.
Torres T, Ferreira EO, Gonçalo M, Mendes-Bastos P, Selores M, Filipe P. Update on Atopic Dermatitis. Acta Med Port. Sep. 2, 2019;32(9):606-613. doi: 10.20344/amp.11963. Epub Sep. 2, 2019. PMID: 31493365.
Salvati L, Cosmi L, Annunziato F. From Emollients to Biologicals: Targeting Atopic Dermatitis. Int J Mol Sci. Sep. 26, 2021;22(19):10381. doi: 10.3390/ijms221910381. PMID: 34638722; PMCID: PMC8508966.
Telofski LS, Morello AP 3rd, Mack Correa MC, Stamatas GN. The infant skin barrier: can we preserve, protect, and enhance the barrier? Dermatol Res Pract. 2012;2012:198789. doi: 10.1155/2012/198789. Epub Sep. 4, 2012. PMID: 22988452; PMCID: PMC3439947.
Kim JP, Chao LX, Simpson EL, Silverberg JI. Persistence of atopic dermatitis (AD): A systematic review and meta-analysis. J Am Acad Dermatol. Oct. 2016;75(4):681-687.e11. doi: 10.1016/j.jaad.2016.05.028. Epub Aug. 17, 2016. PMID: 27544489; PMCID: PMC5216177.
Drucker AM, Wang AR, Li WQ, Sevetson E, Block JK, Qureshi AA. The Burden of Atopic Dermatitis: Summary of a Report for the National Eczema Association. J Invest Dermatol. Jan. 2017;137(1):26-30. doi: 10.1016/j.jid.2016.07.012. Epub Sep. 8, 2016. PMID: 27616422.
Compalati E, Baena-Cagnani R, Penagos M, et al. Systematic review on the efficacy of fexofenadine in seasonal allergic rhinitis: a meta-analysis of randomized, double-blind, placebo-controlled clinical trials. 2011. In: Database of Abstracts of Reviews of Effects (DARE): Quality-assessed Reviews [Internet]. York (UK): Centre for Reviews and Dissemination (UK); 1995 -. Available from: https://www.ncbi.nlm.nih.gov/books/NBK85203/.
Na CH, Chung J, Simpson EL. Quality of Life and Disease Impact of Atopic Dermatitis and Psoriasis on Children and Their Families. Children (Basel). Dec. 2, 2019;6(12):133. doi: 10.3390/children6120133. PMID: 31810362; PMCID: PMC6955769.
Teasdale E, Sivyer K, Muller I, Ghio D, Roberts A, Lawton S, Santer M. Children's Views and Experiences of Treatment Adherence and Parent/Child Co-Management in Eczema: A Qualitative Study. Children (Basel). Feb. 20, 2021;8(2):158. doi: 10.3390/children8020158. PMID: 33672514; PMCID: PMC7923777.
Silverberg JI, Gelfand JM, Margolis DJ, Boguniewicz M, Fonacier L, Grayson MH, Simpson EL, Ong PY, Chiesa Fuxench ZC. Patient burden and quality of life in atopic dermatitis in US adults: A population-based cross-sectional study. Ann Allergy Asthma Immunol. Sep. 2018;121(3):340-347. doi: 10.1016/j.anai.2018.07.006. Epub Jul. 16, 2018. PMID: 30025911.
Ezzedine K, Shourick J, Merhand S, Sampogna F, Taïeb C. Impact of Atopic Dermatitis in Adolescents and their Parents: A French Study. Acta Derm Venereol. Oct. 20, 2020; 100(17):adv00294. doi: 10.2340/00015555-3653. PMID: 33021321; PMCID: PMC9274931.
Beattie PE, Lewis-Jones Ms. A comparative study of impairment of quality of life in children with skin disease and children with other chronic childhood diseases. Br J Dermatol. Jul. 2006; 155(1):145-51. doi: 10.1111/ 1365-2133.2006.07185.x. PMID: 16792766.
Nutten S. Atopic dermatitis: global epidemiology and risk factors. Ann Nutr Metab. 2015;66 Suppl 1:8-16. doi: 10.1159/000370220. Epub Apr. 24, 2015. PMID: 25925336.
Strathie Page S, Weston S, Loh R. Atopic dermatitis in children. Aust Fam Physician. May 2016;45(5):293-6. PMID: 27166464.
Bantz SK, Zhu Z, Zheng T. The Atopic March: Progression from Atopic Dermatitis to Allergic Rhinitis and Asthma. J Clin Cell Immunol. Apr. 2014;5(2):202. doi: 10.4172/2155-9899.1000202. PMID: 25419479; PMCID: PMC4240310.
Aung T, Aung ST. Selection of an effective topical corticosteroid. Aust J Gen Pract. Sep. 2021;50(9):651-655. doi: 10.31128/AJGP-07-20-5507. PMID: 34462770.
Kinnunen T, Koskela M. Antibacterial and antifungal properties of propylene glycol, hexylene glycol, and 1,3-butylene glycol in vitro. Acta Derm Venereol. 1991;71(2):148-50. PMID: 1675525.
Kinnunen T, Koskela M. Antibacterial and antifungal properties of propylene glycol, hexylene glycol, and 1,3-butylene glycol in vitro. Acta Derm Venereol. 1991;71(2):148-50. PMID: 1675525.
Stamatas GN, Nikolovski J, Mack MC, Kollias N. Infant skin physiology and development during the first years of life: a review of recent findings based on in vivo studies. Int J Cosmet Sci. Feb. 2011, 33(1):17-24. doi: 10.1111/i.1468-2494.2010.00611.x. Epub Aug. 30, 2010. PMID: 20807257.
Fluhr, J.W., Darlenski, R., Taieb, A., Hachem, J.-P., Baudouin, C., Msika, P., De Belilovsky, C. and Berardesca, E. (2010), Functional skin adaptation in infancy—almost complete but not fully competent. Experimental Dermatology, 19:483-492. https://doi.org/10.1111/j.1600-0625.2009.01023.x.
Gorski J, Proksch E, Baron JM, Schmid D, Zhang L. Dexpanthenol in Wound Healing after Medical and Cosmetic Interventions (Postprocedure Wound Healing). Pharmaceuticals (Basel). Jun. 29, 2020;13(7):138. doi: 10.3390/ph13070138. PMID: 32610604; PMCID: PMC7407203.
Heena Chaudhary et al., Formulation and Evaluation of fexofenadine hydrochloride transdermal patch, Journal of Drug delivery & therapeutics ; 2012, 2(5), 20-23.
A Pilot Randomized Double Blind Study to Assess the Safety and Efficacy of 1% Ibuprofen/ 1%Fexofenadine Topical Cream for the Treatment of Dark Circles Under the Eye—https://clinicaltrials.gov/ct2/show/NCT01172522.
Zane LT, Hughes MH, Shakib S. Tolerability of Crisaborole Ointment for Application on Sensitive Skin Areas: A Randomized, Double-Blind, Vehicle-Controlled Study in Healthy Volunteers. Am J Clin Dermatol. Oct. 2016;17(5):519-526. doi: 10.1007/s40257-016-0204-6. PMID: 27335049; PMID: PMC5045489.
Schmitt J, Langan S, Deckert S, Svensson A, von Kobyletzki L, Thomas K, Spuls P; Harmonising Outcome Measures for Atopic Dermatitis (HOME) Initiative. Assessment of clinical signs of atopic dermatitis: a systematic review and recommendation. J Allergy Clin Immunol. Dec. 2013;132(6):1337-47. doi: 10.1016/j.jaci.2013.07.008. Epub Sep. 12, 2013. PMID: 24035157.
Nikolovski J, Stamatas GN, Kollias N, Wiegand BC. Barrier function and water-holding and transport properties of infant stratum corneum are different from adult and continue to develop through the first year of life. J Invest Dermatol. Jul. 2008;128(7):1728-36. doi: 10.1038/sj.jid.5701239. Epub Jan. 17, 2008. PMID: 18200056.
Marty O. Visscher, Ralf Adam, Susanna Brink, Mauricio Odio, Newborn infant skin: Physiology, development, and care, Clinics in Dermatology, vol. 33, Issue 3, May-Jun. 2015, pp. 271-280.
Choi JY, Dawe R, Ibbotson S, Fleming C, Doney A, Foerster J. Quantitative analysis of topical treatments in atopic dermatitis: unexpectedly low use of emollients and strong correlation of topical

(56) References Cited

OTHER PUBLICATIONS corticosteroid use both with depression and concurrent asthma. Br J Dermatol. Apr. 2020;182(4):1017-1025. doi: 10.1111/bjd. 18265. Epub Sep. 15, 2019. PMID: 31257575.

Mason J, Reynolds R, Rao N. The systemic safety of fexofenadine HCI. Clin Exp Allergy. Jul. 1999; 29 Suppl 3:163-70; discussion 171-3. doi: 10.1046/j.1365-2222.1999.0290s3163.x. PMID: 10444232.

Phinyo P, Koompawichit P, Nochaiwong S, Tovanabutra N, Chiewchanvit S, Chuamanochan M. Comparative Efficacy and Acceptability of Licensed Dose Second-Generation Antihistamines in Chronic Spontaneous Urticaria: A Network Meta-Analysis. J Allergy Clin Immunol Pract. Feb. 2021;9(2):956-970.e57. doi: 10.1016/j.jaip.2020.08.055. Epub Sep. 8, 2020. PMID: 32916325.

* cited by examiner

TOPICAL FORMULATIONS AND COMPOSITIONS

PRIORITY

The present application is a continuation of International Patent Application No. PCT/IB2022/051367, which was filed Feb. 16, 2022, which claims benefit of Indian provisional Application No. 202141048441 filed on Oct. 24, 2021, Indian provisional Application No. 202141016620 filed on Apr. 8, 2021, and Indian provisional Application No. 202141006680 filed on Feb. 17, 2021, the entire disclosures of which are relied on for all purposes and are incorporated into the application by reference.

FIELD OF THE INVENTION

The present disclosure generally relates to the field of pharmaceutical compositions. In particular, the present disclosure provides a topical formulation that includes fexofenadine or a salt or a hydrate or a solvate thereof. The compositions of the present disclosure may find utility in treatment of allergic conditions/diseases.

BACKGROUND OF THE INVENTION

Inflammation is a biological response of the immune system that can be triggered by various infectious, immunological, physical, chemical, and inert agents. These factors may induce inflammatory responses in the organs leading to tissue damage or disease.

Allergic diseases, such as rashes, urticarial flares, itching, tick bites, eczema, and keratosis are inflammatory, itchy skin diseases are due to a complex interaction between several inflammatory cells in response to various environmental/allergic stimuli. These cells produce an abundance of inflammatory mediators. Mast cell histamine is an axial player in stimulating the development of allergic-related inflammatory diseases by regulating the maturation and activation of leukocytes and directing their migration to target sites where they cause chronic inflammation. Most of the population in United States affected by skin diseases causing considerable morbidity, poor quality of life, and high medical costs.

Psoriasis is also a chronic pruritic inflammatory skin disease and is a long-term (chronic) disease. Inflammation and the tumor necrosis factor (TNF-alpha) are important in innate immune responses and is increased in psoriatic lesions. Treatment depends on how severe the psoriasis is and how responsive it has been to previous treatment. Topical corticosteroids, vitamin D analogues, retinoids, calcineurin inhibitors, salicylic acid, either by themselves or in combination with phototherapy or systemic agents (such as methotrexate, cyclosporine, other medications include thioguanine and hydroxyurea, etc.), have been used for therapy. However, these agents can be extremely expensive. Prolonged use of topical steroids can cause systemic side effects.

Histamine plays important roles in inflammation and nervous irritability in allergic skin disorders, including atopic dermatitis, urticaria, and itching conditions. Itching is often triggered by histamine, a chemical in the body associated with immune responses. Histamine is released from mast cells when tissues are inflamed or stimulated by allergens, and once released, histamine induces itch is triggered by the excitation of a subset of unmyelinated C-fibers. It causes the itch and redness by tick bites, rashes and skin damage. H1R antagonism does, at least to some extent, attenuate histamine-induced itch, because non-sedative second generation H1R antihistamines are beneficial for the management of itch symptoms. Histamine is one of the major mediators of most forms of urticaria although in some cases, especially physical urticaria, other mediators seem to play a role. Therefore antihistamines, and mainly H1 antihistamines, are the mainstay of anti-urticaria therapy. Further, not all H1 antihistamines inhibit the inflammatory response that results from the release of histamine in humans.

Although numerous compositions have been reported so far, they suffer from one or more shortcomings. There is, therefore, a need for improved compositions and methods that can be used to treat a wide variety of allergic diseases/disorders of skin. A need is also felt of improved formulations that are easy to administer and aids in improving patient compliance. The present disclosure satisfies the existing needs, at least in part, and overcomes one or more disadvantages of the conventional approaches.

OBJECTS OF THE INVENTION

One of the objects of the present disclosure is to provide a pharmaceutical composition that may overcome one or more limitations associated with the conventional compositions.

Yet another object of the present disclosure is to provide a pharmaceutical composition that finds utility in treatment for a wide variety of allergic diseases/conditions.

Further object of the present disclosure is to provide a pharmaceutical composition that exhibit improved efficacy and devoid any side-effects.

One of the objects of the present disclosure is to improve the stability of fexofenadine HCl with improved topical bioavailability and delivery.

Further object of the present disclosure is to provide a pharmaceutical composition that is easy to prepare and is economical.

SUMMARY OF THE INVENTION

The present disclosure generally relates to the field of pharmaceutical compositions. In particular, the present disclosure provides a topical formulation that includes H1 antagonist or a salt or a hydrate or a solvate thereof. The compositions of the present disclosure may find utility in treatment of allergic conditions/diseases.

Present disclosure provides a pharmaceutical composition comprising H1 antagonist or a salt or a hydrate or a solvate thereof in an amount broadly ranging from 0.0001% to 20% w/w.

An aspect of the present disclosure provides a pharmaceutical composition including: fexofenadine or a salt or a hydrate or a solvate thereof in an amount ranging from 0.001% to 10% w/w: a diluent in an amount ranging from 30% to 80% w/w; a solvent in an amount ranging from 1% to 30% w/w; an emollient in an amount ranging from 10% to 40% w/w; a humectant in an amount ranging from 5% to 30% w/w; a preservative in an amount ranging from 0.1% to 15% w/w; an emulsifier in an amount ranging from 0.1% to 10% w/w; and a surfactant in an amount ranging from 2% to 30% w/w, said composition being formulated as a topical formulation.

An another aspect of the present disclosure provides a pharmaceutical composition including: diphenhydramine or a salt or a hydrate or a solvate thereof in an amount ranging from 0.001% to 10% w/w: a diluent in an amount ranging from 30% to 80% w/w: a solvent in an amount ranging from 1% to 30% w/w; an emollient in an amount ranging from 10% to 40% w/w; a humectant in an amount ranging from 5% to 30% w/w; a preservative in an amount ranging from 0.1% to 15% w/w; an emulsifier in an amount ranging from 0.1% to 10% w/w; and a surfactant in an amount ranging from 2% to 30% w/w, said composition being formulated as a topical formulation.

In yet another aspect of the present disclosure provides a pharmaceutical composition comprising one or more than one H1 antagonist alone or in combination.

In some embodiment H1 antagonist is selected from fexofenadine, diphenhydramine, cetirizine, levocetirizine, montelukast or a combination thereof.

In still another aspect of the present disclosure provides a pharmaceutical composition may include an H1 antagonist and a second or third active agent.

In an embodiment, the diluent is water. In an embodiment, the solvent is selected from ethanol, butylene glycol, propylene glycol, isopropyl alcohol, isoprene glycol, benzyl alcohol, Cremophor EL and combinations thereof. In an embodiment, the emollient is selected from white petrolatum, light and heavy mineral oil, triglycerides, silicon, dimethicone, isopropyl myristate, cetyl alcohol and combinations thereof. In an embodiment, the humectant is selected from glycerin, glycerol, propylene glycol, butylene glycol, sorbitol, polyethylene glycol and combinations thereof. In an embodiment, the surfactant is selected from Polysorbate 20, Polysorbate 40, Polysorbate 60, Polysorbate 80, Span 20, Span 40, Span 60, Span 80, lauramide DEA, cocamide DEA, Kollicream® IPM, triethylamine [TEA], cocamide MEA, glyceryl monostearate, stearic acid, polyethylene glycol ether of cetearyl alcohol, lauroyl polyoxyl-32 glycerides and combinations thereof. In an embodiment, the composition further includes a skin penetration enhancer in an amount ranging from 0.01% to 10% w/w. In an embodiment, the composition further includes a preservative in an amount ranging from 0.1% to 5% w/w. In an embodiment, the composition is formulated as a topical lotion.

In an embodiment, the composition further comprises an active agent selected from a steroid, a PDE 4 inhibitor, an anti-inflammatory agent, an immunosuppressant, an antibiotic, an antifungal, a non-steroidal anti-inflammatory agent, a retinoid agent, an antipruritic agent and combinations thereof.

In an embodiment, the composition is formulated as a solution, spray, lotion, cream, gel, ointment, or as an emulsion, oil in water emulsion, water in oil emulsion for topical, dermal or transdermal administration.

In another embodiment, present invention provides a composition for topical treatment of allergic condition comprising: H1 antihistamine or a salt or a hydrate or a solvate thereof, a diluent, a solvent, an emollient, a humectant, emulsifier, emulsion stabilizer, preservative, penetration enhancers, stiffening agents, a surfactant and one or more additional excipients; wherein the allergic condition is atopic contact dermatitis, eczema, urticaria, psoriasis, angioedema, hereditary angioedema or the combination thereof.

In some embodiment, present invention provides a composition for topical treatment of allergic condition comprising: H1 antihistamine or a sak or a hydrate or a solvate thereof, a solvent/co-solvent, an emollient, emulsifier, emulsion stabilizer, preservative, diluent and optional fragrance.

The allergic condition is atopic contact dermatitis, eczema, urticaria, psoriasis, angioedema, hereditary angioedema or the combination thereof.

Another aspect of the present disclosure relates to a method of treating an allergic condition in a patient in need thereof comprising applying to a subject a therapeutically effective amount of the composition.

Still another aspect of the present disclosure relates to the use of the pharmaceutical composition in the preparation of a medicament for the treatment of an allergic condition in patient in need thereof.

The advantageous topical formulation of the present disclosure upon application on skin releases H1 histamine such as fexofenadine and or diphenhydramine locally in a sustained manner while providing moisturizing effect. The advantageous topical formulation of the present disclosure forms a thin layer on the skin, which acts like a barrier and prevent entry of pathogens and allergens into the deep layers of skin. Accordingly, the formulations of the present disclosure can find utility in treatment of a wide variety of allergic conditions/diseases/disorders related to skin.

DETAILED DESCRIPTION OF THE INVENTION

Figure 1:
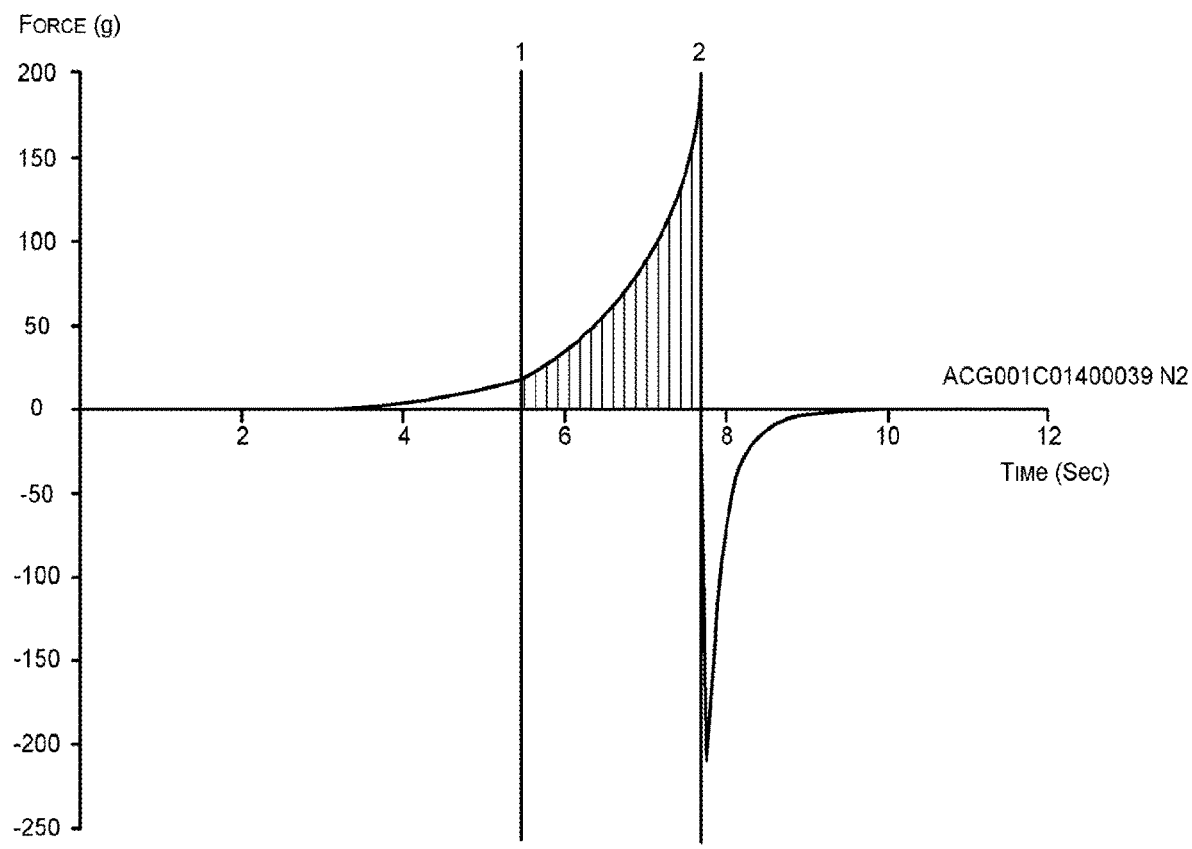
FIG. 1: Texture plot of batch ACG001C0140039

As used herein, the following terms and phrases shall have the meanings set forth below. Unless defined otherwise, all technical and scientific terms used herein have the same meaning as commonly understood to one of ordinary skill in the art. It is also understood that the terminology used herein is for the purpose of describing particular embodiments only and is not intended to be limiting.

It must be noted that, as used in this specification and the appended claims, the singular forms "a," "an" and "the" include plural referents unless the context clearly dictates otherwise. Thus, for example, "an active agent" or "an active ingredient" refers not only to a single active agent but also to a combination of two or more different active agents, "a dosage form" refers to a combination of dosage forms as well as to a single dosage form, and the like.

The term "active agent" or "therapeutic agent", encompass not only the specified molecular entity but also its pharmaceutically acceptable, pharmacologically active analogs, including, but not limited to, salts, esters, amides, prodrugs, conjugates, active metabolites, and other such derivatives, analogs, and related compounds.

The terms "treating" and "treatment" as used herein refers to reduction in severity and/or frequency of symptoms, elimination of symptoms and/or underlying cause, and improvement or remediation of damage caused thereby. Thus, "treating" a subject/patient as described herein encompasses treating a wide variety of allergic conditions such as atopic contact dermatitis rashes, inflammation, urticarial flares, urticaria, angioedema, hereditary angioedema, itching, tick bites, psoriasis, eczema and keratosis, but not limited thereto, which may be triggered upon a subject on coming into contact with allergen(s).

The term "pharmaceutically acceptable" means the material incorporated into a pharmaceutical composition that can be administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the regulatory authority.

The present disclosure generally relates to the field of pharmaceutical compositions. In particular, the present disclosure provides a topical formulation that includes H1 antagonist or a salt or a hydrate or a solvate thereof. The compositions of the present disclosure may find utility in treatment of allergic conditions/diseases. The advantageous topical formulation of the present disclosure upon application on skin releases H1 antagonist locally in a sustained manner while providing moisturizing effect. Further, the advantageous topical formulation of the present disclosure further forms a thin layer on the skin, which acts like a barrier and prevent entry of pathogens and allergens into the deep layers of skin.

Present topical composition comprising H1 antihistamines/H1 antagonist/H1 receptor blockers are very effective because the H1 receptor are strongly expressed in the epidermis and topical application of H1 antagonist improve barrier function in normal skin also improve bioavailability and efficacy of antihistamines when applied topical to treat inflammatory skin conditions, with or without associated barrier abnormalities. H1 antihistamines down-regulate allergic inflammation through the H1 receptor, either directly or indirectly through nuclear factor-κB, a ubiquitous transcription factor, through which they down-regulate antigen presentation, expression of pro-inflammatory cytokines and cell adhesion molecules, chemotaxis, leukotrienes or cytokines. In addition, through their effects on calcium ion channel activity, H1 antihistamines decrease mediator release.

Fexofenadine in the composition has low plasma-protein binding thus having high affinity for H1 receptors. The composition as disclosed here are effective therapy not only through enhanced anti-inflammatory activity but also partly through their ability to improve epidermal structure and function. H1 antagonist improved the epidermal differentiation, leading to more robust corneocytes formation and lipid secretion thus improving the barrier function of the skin.

An aspect of the present disclosure provides a pharmaceutical composition including: fexofenadine or a sak or a hydrate or a solvate thereof in an amount ranging from 0.001% to 10% w/w; a diluent in an amount ranging from 30% to 80% w/w; a solvent in an amount ranging from 1% to 30% w/w; an emollient in an amount ranging from 10% to 40% w/w; a humectant in an amount ranging from 5% to 30% w/w: a preservative in an amount ranging from 0.1% to 15% w/w; an emulsifier in an amount ranging from 0.1% to 10% w/w; and a surfactant in an amount ranging from 2% to 30% w/w, said composition being formulated as a topical formulation.

In an embodiment, the composition of the present disclosure comprises fexofenadine or a salt or a hydrate or a solvate thereof in an amount ranging from 0.2% to 8% w/w.

In an alternative embodiment, the composition of the present disclosure comprises fexofenadine or a salt or a hydrate or a solvate thereof in an amount ranging from 0.5% to 5% w/w.

An another aspect of the present disclosure provides a pharmaceutical composition including: diphenhydramine or a salt or a hydrate or a solvate thereof in an amount ranging from 0.001% to 10% w/w; a diluent in an amount ranging from 30% to 80% w/w; a solvent in an amount ranging from 1% to 30% w/w: an emollient in an amount ranging from 10% to 40% w/w; a humectant in an amount ranging from 5% to 30% w/w: a preservative in an amount ranging from 0.1% to 15% w/w; an emulsifier in an amount ranging from 0.1% to 10% w/w; and a surfactant in an amount ranging from 2% to 30% w/w, said composition being formulated as a topical formulation.

In an embodiment, the composition of the present disclosure comprises diphenhydramine or a salt or a hydrate or a solvate thereof in an amount ranging from 0.2% to 8% w/w. In an alternative embodiment, the composition of the present disclosure comprises diphenhydramine or a salt or a hydrate or a solvate thereof in an amount ranging from 0.5% to 5% w/w.

In yet another aspect of the present disclosure provides a pharmaceutical composition comprising H1 antagonist alone or in combination of 2 or more.

In still another aspect of the present disclosure provides a pharmaceutical composition may include an H1 antagonist and a second or a third active agent.

In an embodiment, the non-limiting examples of H1 antagonist include acrivastine, alimemazine, amitriptyline, amoxapine, azelastine, bilastine, bromodiphenhydramine, brompheniramine, buclizine, carbinoxamine, cetirizine, chlorodiphenhydramine, chlorpheniramine, chlorpromazine, chlorprothixene, chloropyramine, cinnarizine, clemastine, clomipramine, clozapine, cyclizine, cyproheptadine, desloratadine, dexbrompheniramine, dexchlorpheniramine, dimenhydrinate, dimetindene, diphenhydramine, dosulepin, doxepin, doxylamine, ebastine, embramine, hydroxyzine, imipramine, levocabastine, levocetirizine, levomepromazine, loratadine, maprotiline, meclizine, mianserin, mirtazapine, montelukast, olanzapine, olopatadine, orphenadrine, periciazine, phenindamine, pheniramine, phenyltoloxamine, promethazine, pyrilamine, quetiapine, rupatadine, terfenadine, trazodone, tripelennamine, triprolidine In an embodiment, the composition further comprises a pharmaceutically active agent selected from a corticosteroid, a H1 antagonist, phosphodiesterase (PDE)inhibitor, NO— release drug, UV— filter/sun block agents, an anti-inflammatory agent, an immunosuppressant, an antibiotic, an anti-fungal agent, a non-steroidal anti-inflammatory agent, a retinoid agent, an antipruritic agent, a keratolytic agent, JAK inhibitors and combinations thereof.

Non-limiting examples of steroids include: amcinonide, alclometasone dipropionate, betamethasone dipropionate, betamethasone valerate, clocortolone pivalate, clobetasone, clobetasol propionate, desoximetasone, diflucortolone valerate, desonide, halobetasol, diflorasone, diflorasone diacetate, propionate, flurandrenolide, fluocinonide, fluocinolone acetonide, halcinonide, hydrocortisone acetate, hydrocortisone valerate, hydrocortisone butyrate, hydrocortisone probutate, mometasone furoate, mapracorat, hydrocortisone acetate, methylprednisolone, prednicarbate, prednisolone, pefcalcitol, triamcinolone acetonide and combinations thereof.

Non-limiting examples of anti-inflammatory agents include methotrexate, ciclosporin, vitamin D analogues like calcipotriol and combinations thereof.

Non-limiting examples of calcineurin inhibitors include tacrolimus, pimecrolimus, vitamin B3 or derivatives thereof and combinations thereof.

Non-limiting examples of non-steroidal anti-inflammatory agents include diclofenac, indomethacin, sulindac, mefenamic acid, piroxicam, ibuprofen, ketoprofen, naproxen, phenylbutazone, meloxicam, nimesulide, celecoxib, etoricoxib WBI-1001, MRX-6, valdecoxib and combinations thereof.

Non-limiting examples of retinoid agents include azarotene, isotretinoin, adapalene, tretinoin and combinations thereof. Non-limiting examples of antipruritics agents include crotampiton. Other active agent can also be included as part of the composition such as, but not limited to, keratolytic agents such as salicylic acid: urea-containing preparations and alphahydroxy acids, such as glycolic and lactic acids; an antibiotic agent such as cyclosporines, erythromycin, quinolones, fluoroquinolnes and clindamycin; an antifungal agent such as di and triazoles, miconazole, fluconazole, ketoconazole, voriconazole, clotrimazole, itraconazole griseofulvin, ciclopirox, amorolfine and terbinafine.

Non-limiting examples of UV-filter include p-aminobenzoic acid, padimate o, phenylbenzimidazole sulfonic acid, cinoxate, dioxybenzone, oxybenzone, homosalate, menthyl anthranilate, octocrylene, octyl methoxycinnamate, octyl salicylate, sulisobenzone, trolamine salicylate, avobenzone, ecamsule, titanium dioxide and zinc oxide.

Non-limiting examples of immunosuppressant include azathioprine, mycophenolic acid, leflunomide, terifluno-mide, ciclosporin, pimecrolimus, tacrolimus, voclosporin, lenalidomide, pomalidomide, thalidomide, apremilast, sirolimus, everolimus, ridaforolimus, temsirolimus, umirolimus, zotarolimus, baricitinib, blisibimod, nilotinib, filgotinib, tofacitinib, upadacitinib, abatacept, belatacept, etanercept pegsunercept, aflibercept, alefacept and rilonacept.

Non-limiting examples of NO releasing drugs include glyceryl trinitrate, isosorbide dinitrate, isosorbide mononitrate, isoamyl nitrite and other derivatives and analogs with the NO releasing properties.

Non-limiting examples of PDE inhibitors include PDE 4 such as apremilast, arofylline, atizoram, benafentrine, catramilast, CC-1088, CDP-840, CGH-2466, cilomilast, cipamfylline, crisaborole, denbutylline, difamilast, drotaverine, etazolate, filaminast, glaucine. HT-0712, ICI-63197, indimilast, irsogladine, lavamilast, lirimilast, lotamilast, luteolin, mesembrenone, mesembrine, mesopram, oglemilast, piclamilast, pumafentrine, revamilast, Ro 20-1724, RVT-501, DRM02, OPA-15406, LEO-29102, HFP034, butyl 2-[2-(2-fluorophenyl) acetamido] benzoate, roflumilast, rolipram, ronomilast, RPL-554, RS-25344, tetomilast, tofimilast, YM-976, zardaverine, ibudilast, roflumilast; PDE 3 Inhibitors such as adibendan, amrinone (inamrinone), anagrelide, benafentrine, bucladesine, carbazeran, cilostamide, cilostazol, enoximone, imazodan, KMUP-1, meribendan, milrinone, olprinone, parogrelil, pimobendan, pumafentrine, quazinone, RPL-554, siguazodan, trequinsin, vesnarinone, zardaverine; PDE 5 inhibitors such as acetildenafil, aildenafil, avanafil, beminafil, benzamidenafil, dasantafil, icariin, gisadenafil, homosildenafil, lodenafil, mirodenafil, MY-5445, nitrosoprodenafil, norcarbodenafil, SCH-51866, sildenafil, sulfoaildenafil, T-0156, tadalafil, udenafil, and vardenafil or combination thereof.

Non-limiting examples of JAK inhibitor agents include baricitinib, tofacitinib, delgocitinib, upadacitinib, abrocitinib and gusacitinib or a combination thereof.

In an embodiment the topical composition comprises of H1 antihistamine or a salt or a hydrate or a solvate thereof, a diluent, a solvent/co-solvent, an emollient, a humectant, a emulsifier, emulsion stabilizer, penetration enhancers, preservatives, stiffening agents, a surfactant and one or more additional excipient (composition 1).

In an embodiment the topical composition comprises of fexofenadine HCl or a sat or a hydrate or a solvate thereof, a diluent, a solvent, an emollient, a humectant, and a surfactant.

In an embodiment the topical composition comprises of diphenhydramine HCl or a salt or a hydrate or a solvate thereof, a diluent, a solvent, an emollient, a humectant, and a surfactant.

FURTHER EMBODIMENTS

Composition 1a: Composition 1 in combination with antimicrobial agents (antibiotic agents or antifungal agent or antiviral agents or anti-infective agents).

Composition 1b: Composition 1 in combination with corticosteroid.

Composition 1c: composition 1 in combination with immunosuppressant.

Composition 1d: composition 1 in combination with NO releasing drugs.

Composition 1e: composition 1 in combination with PDE inhibitors.

Composition 1f: composition 1 in combination with anti-inflammatory agents.

Composition 1g: composition 1 in combination with a retinoid agent.

Composition 1h: composition 1 in combination with an antipruritic agent.

Composition 1i: composition 1 in combination with a keratolytic agent.

Composition 2a: Composition 1a in combination with corticosteroid.

Composition 2b: composition 1a in combination with immunosuppressant.

Composition 2c: composition 1a in combination with NO releasing drugs.

Composition 2d: composition 1a in combination with PDE inhibitors.

Composition 2e: composition 1a in combination with anti-inflammatory agents.

Composition 2f: composition 1a in combination with a retinoid agent.

Composition 2g: composition 1a in combination with an antipruritic agent.

Composition 2h: composition 1a in combination with a keratolytic agent.

Composition 3a: Composition 1b in combination with antimicrobial agents.

Composition 3b: composition 1b in combination with immunosuppressant.

Composition 3c: composition 1b in combination with NO releasing drugs.

Composition 3d: composition 1b in combination with PDE inhibitors.

Composition 3e: composition 1b in combination with anti-inflammatory agents.

Composition 3f: composition 1b in combination with a retinoid agent.

Composition 3g: composition 1b in combination with an antipruritic agent.

Composition 3h: composition 1b in combination with a keratolytic agent.

Composition 4a: Composition 1c in combination with antimicrobial agents.

Composition 4b: composition 1c in combination with corticosteroid.

Composition 4c: composition 1c in combination with NO releasing drugs.

Composition 4d: composition 1c in combination with PDE inhibitors.

Composition 4e: composition 1c in combination with anti-inflammatory agents.

Composition 4f composition 1c in combination with a retinoid agent.

Composition 4g: composition 1c in combination with an antipruritic agent.

Composition 4h: composition 1c in combination with a keratolytic agent.

Composition 5a: Composition 1d in combination with antimicrobial agents.

Composition 5b: composition 1d in combination with corticosteroid.

Composition 5c: composition 1d in combination with immunosuppressant.

Composition 5d: composition 1d in combination with PDE inhibitors.

Composition 5e: composition 1d in combination with anti-inflammatory agents.

Composition 5f: composition 1d in combination with a retinoid agent.

Composition 5g: composition 1d in combination with an antipruritic agent.

Composition 5h: composition 1d in combination with a keratolytic agent.

Composition 6a: Composition 1e in combination with antimicrobial agents.

Composition 6b: composition 1e in combination with corticosteroid.

Composition 6c: composition 1e in combination with immunosuppressant.

Composition 6d: composition 1e in combination with NO releasing drugs.

Composition 6e: composition 1e in combination with anti-inflammatory agents.

Composition 6f: composition 1e in combination with a retinoid agent.

Composition 6g: composition 1e in combination with an antipruritic agent.

Composition 6h: composition 1e in combination with a keratolytic agent.

Composition 7a: Composition 1f in combination with antimicrobial agents.

Composition 7b: composition 1f in combination with corticosteroid.

Composition 7c: composition 1f in combination with immunosuppressant.

Composition 7d: composition 1f in combination with NO releasing drugs.

Composition 7e: composition 1f in combination with PDE inhibitors.

Composition 7f: composition 1f in combination with a retinoid agent.

Composition 7g: composition 1f in combination with an antipruritic agent.

Composition 7h: composition 1f in combination with a keratolytic agent.

Composition 8a: Composition 1g in combination with antimicrobial agents.

Composition 8b: composition 1g in combination with corticosteroid.

Composition 8c: composition 1g in combination with immunosuppressant.

Composition 8d: composition 1g in combination with NO releasing drugs.

Composition 8e: composition 1g in combination with PDE inhibitors.

Composition 8f: composition 1g in combination with an anti-inflammatory agent.

Composition 8g: composition 1g in combination with an antipruritic agent.

Composition 8h: composition 1g in combination with a keratolytic agent.

Composition 9a: Composition 1h in combination with antimicrobial agents.

Composition 9b: composition 1h in combination with corticosteroid.

Composition 9c: composition 1h in combination with immunosuppressant.

Composition 9d: composition 1h in combination with NO releasing drugs.

Composition 9e: composition 1h in combination with PDE inhibitors.

Composition 9f: composition 1h in combination with a retinoid agent.

Composition 9g: composition 1h in combination with an anti-inflammatory agents.

Composition 9h: composition 1h in combination with a keratolytic agent.

In an embodiment, the composition of the present disclosure comprises a H1 antihistamine, a antimicrobial agent, a diluent, a solvent, an emollient, a humectant, and a surfactant.

In an embodiment, the composition of the present disclosure comprises a H1 antihistamine, corticosteroid, a diluent, a solvent, an emollient, a humectant, and a surfactant.

In an embodiment, the composition of the present disclosure comprises a H1 antihistamine, PDE inhibitor, a diluent, a solvent, an emollient, a humectant, and a surfactant.

In an embodiment, the composition of the present disclosure comprises a H1 antihistamine, NO— release drug, a diluent, a solvent, an emollient, a humectant, and a surfactant.

In an embodiment, the composition of the present disclosure comprises a H1 antihistamine, UV— filter/sun block agents, a diluent, a solvent, an emollient, a humectant, and a surfactant.

In an embodiment, the composition of the present disclosure comprises a H1 antihistamine, an anti-inflammatory agent, a diluent, a solvent, an emollient, a humectant, and a surfactant.

In an embodiment, the composition of the present disclosure comprises a H1 antihistamine, an immunosuppressant, a diluent, a solvent, an emollient, a humectant, and a surfactant.

In an embodiment, the composition of the present disclosure comprises a H1 antihistamine, a retinoid agent, a diluent, a solvent, an emollient, a humectant, and a surfactant.

In an embodiment, the composition of the present disclosure comprises a H1 antihistamine, an antipruritic agent, a diluent, a solvent, an emollient, a humectant, and a surfactant.

In an embodiment, the composition of the present disclosure comprises a H1 antihistamine, keratolytic agent, a diluent, a solvent, an emollient, a humectant, and a surfactant.

In an embodiment, the composition of the present disclosure comprises a H1 antihistamine, an antimicrobial agent, a corticosteroid, a diluent, a solvent, an emollient, a humectant, and a surfactant.

In an embodiment, the composition of the present disclosure comprises a H1 antihistamine, a antimicrobial agent, PDE inhibitor, a diluent, a solvent, an emollient, a humectant, and a surfactant.

In an embodiment, the composition of the present disclosure comprises a H1 antihistamine, an antimicrobial agent, NO— release drug, a diluent, a solvent, an emollient, a humectant, and a surfactant.

In an embodiment, the composition of the present disclosure comprises a H1 antihistamine, an antimicrobial agent, anti-inflammatory agent, a diluent, a solvent, an emollient, a humectant, and a surfactant.

In an embodiment, the composition of the present disclosure comprises a H1 antihistamine, an antimicrobial agent, an immunosuppressant, a diluent, a solvent, an emollient, a humectant, and a surfactant.

In an embodiment, the composition of the present disclosure comprises a H1 antihistamine, an antimicrobial agent, a antipruritic agent, a diluent, a solvent, an emollient, a humectant, and a surfactant.

In an embodiment, the composition of the present disclosure comprises a H1 antihistamine, an antimicrobial agent, an antipruritic agent. PDE inhibitor, a diluent, a solvent, an emollient, a humectant, and a surfactant.

In an embodiment, the composition of the present disclosure comprises a diluent in an amount ranging from 35% to 75% w/w. In an alternative embodiment, the composition of the present disclosure comprises a diluent in an amount ranging from 40% to 70% w/w. In another embodiment, the formulation composition may be aqueous or non-aqueous. In an embodiment, the diluent includes any aqueous medium including water. In certain embodiment, the diluent is water.

In an embodiment, the composition of the present disclosure comprises a solvent in an amount ranging from 2% to 25% w/w. In an alternative embodiment, the composition of the present disclosure comprises a solvent in an amount ranging from 1% to 20% w/w. Non-limiting examples of solvent includes, organic solvents such as alcohols (particularly lower alcohols readily capable of evaporating from the skin such as ethanol), glycols (such as propylene glycol, butylene glycol, and glycerin), aliphatic alcohols (such as lanolin); mixtures of water and organic solvents (such as water and alcohol), and mixtures of organic solvents such as alcohol and glycerin (optionally also with water) and combinations thereof. In an embodiment, the solvent is selected from ethanol, butylene glycol, propylene glycol, isopropyl alcohol, isoprene glycol, benzyl alcohol, Cremophor EL and combinations thereof.

In an embodiment, the composition of the present disclosure comprises an emollient in an amount ranging from 12% to 35% w/w. In an alternative embodiment, the composition of the present disclosure comprises an emollient in an amount ranging from 15% to 30% w/w. Non-limiting examples of emollient includes, PPG-IS stearyl ether, lanolin alcohol, lanolin, lanolin derivatives, cholesterol, petrolatum, isostearyl neopentanoate, octyl stearate, mineral oil, isocetyl stearate, Ceraphyl 424 (myristyl myristate), octyl dodecanol, dimethicone (Dow Corning 200-100 cps), phenyl trimethicone (Dow Corning 556), Dow Corning 1401 (cyclomethicone and dimethiconol), and cyclomethicone (Dow Corning 344), and Miglyol 840 (manufactured by Huls; propylene glycol dicaprylate/dicaprate) triglycerides, silicon, and dimethicone, or a combinations thereof. In an embodiment, the emollient is selected from white petrolatum, mineral oil, isopropyl myristate, cetyl alcohol and combinations thereof.

In an embodiment, the composition of the present disclosure comprises humectant in an amount ranging from 7% to 25% w/w. In an alternative embodiment, the composition of the present disclosure comprises the humectant in an amount ranging from 5% to 20% w/w. In an embodiment, the humectant is selected from glycerin, glycerol, propylene glycol, butylene glycol, sorbitol, polyethylene glycol and combinations thereof.

In an embodiment, the composition of the present disclosure comprises a surfactant in an amount ranging from 4% to 25% w/w. In an alternative embodiment, the composition of the present disclosure comprises a surfactant in an amount ranging from 2% to 25% w/w. Non-limiting examples of surfactant includes, Gelucire 44/14, CERALUTION® H, BIOBASE® EP, glyceryl monostearate, solid fatty alcohols, sorbitan trioleate, fatty esters, glyceryl stearate, or any combinations thereof. CERALUTION® H is available from Sasol and includes behenyl alcohol, glyceryl stearate, glyceryl stearate citrate, and sodium dicocoylethylenediamine PEG-15 sulfate. BIOBASE® EP is available from Tri-K and includes glyceryl stearate, cetearyl alcohol, sodium lauroyl lactylate, and lecithin. In an embodiment, the surfactant is selected from Polysorbate 20, Polysorbate 40, Polysorbate 60, Polysorbate 80, Span 20, Span 40, Span 60, Span 80, lauramide DEA, cocamide DEA, Kollicream® IPM, triethylamine [TEA], cocamide MEA, glyceryl monostearate, stearic acid, polyethylene glycol ether of cetearyl alcohol, lauroyl polyoxyl-32 glycerides, fatty acid derivatives such as diglyceryl lauryl fumarate (DGLF), diglyceryl lauryl succinate (DGLS), diglyceryl capryl succinate (DGCS), diglyceryl capryl fumarate (DGCF) and combinations thereof. Diglyceryl lauryl fumarate (DGLF), diglyceryl lauryl succinate, diglyceryl capryl succinate and/or diglyceryl capryl fumarate may be used in the composition to improve delivery of active agents.

In certain aspects, the composition may include one more additional excipients general used in the topical formulations. These excipients are selected in a specific ratio or mixtures from Glyceryl monostearate 40, Macrogol cetostearyl ether 12, cetyl alcohol, stearyl alcohol, cetostearyl alcohol, cetostearyl alcohol 50, ceteareth 20, sorbitan stearate, steareth, polyoxyl cetostearyl ethers, lecithin, methyl cellulose, polyoxyl 20, cetostearyl ether (ceteareth 20), ethylcellulose, hard paraffin wax, microcrystalline wax, hydroxymethylcellulose, hydroxypropylcellulose, polyvinylpyrrolidone, polyvinyl alcohol, acrylic polymers, cetyl acid, stearic acid, lauric acid, myristic acid, erucic acid, palmitic acid, palmitoleic acid, capric acid, caprylic acid, oleic acid, linoleic acid, linolenic acid, hydroxystearic acid, 12-hydroxystearic acid, cetostearic acid, isostearic acid, sesquioleic acid, sesqui-9-octadecanoic acid, sesquiisooctadecanoic acid, behenic acid, isobehenic acid, arachidonic acid, aliphatic alcohol that is saturated or unsaturated, mixture of different fatty alcohols, stearyl alcohol, lauryl alcohol, palmityl alcohol, cetyl alcohol, capryl alcohol, caprylyl alcohol, oleyl alcohol, linolenyl alcohol, arachidonic alcohol, behenyl alcohol, isobehenyl alcohol, selachyl alcohol, chimyl alcohol, linoleyl alcohol, polyalkylene glycol, polyethylene glycol, polyethoxylated sorbitan esters, polyethoxylated sorbitan ester, sorbitan esters, the Span™ series (available from Uniqema), sorbitan monolaurate, sorbitan monopalmitate, sorbitan monostearate, sorbitan tristearate, sorbitan monooleate, sorbitan trioleate, polyethoxylated sorbitan esters, Tween™ series (available from Uniqema), Tween 20 (POE(20) sorbitan monolaurate), 21 (POE(4) sorbitan monolaurate), 40 (POE(20) sorbitan monopalmitate), 60 (POE(20) sorbitan monostearate), 60K (POE(20) sorbitan monostearate), 61 (POE(4) sorbitan monostearate), 65 (POE(20) sorbitan tristearate), 80 (POE(20) sorbitan monooleate), 80K (POE(20) sorbitan monooleate), 81 (POE (5) sorbitan monooleate), and 85 (POE(20) sorbitan trioleate), glyceryl fatty esters, mono-, di- or triglycerides of fatty acids, alkylene glycol, propylene glycol (1,2-propanediol), polyethylene glycol, derivatives of polyethylene glycols, polyethylene glycol-200, polyethylene glycol-300, polyethylene glycol-400, polyethylene glycol-600, and polyethylene glycol-900, paraben, methyl paraben, propyl paraben or a combination thereof. These excipients may have multiple functions in the composition they can be an emulsifiers or emulsion stabilizers or viscosity modifier or stiffening agent or a surfactant and other functions that are known in the art. In an embodiment, the composition includes the emulsifier in an amount ranging from 0.1% to 10% w/w.

In an embodiment, the composition further includes a skin penetration enhancer, a preservative, a moisturizing agent, a film former/waterproofing agent, a pH adjuster/chelating agent, a rheology modifying agent, a fragrance, a colorant, a vitamin, and any combinations thereof.

In some embodiments, the composition further comprises an occlusive agent selected from fatty acids (e.g., lanolin acid), fatty alcohols (e.g., lanolin alcohol), hydrocarbon oils & waxes (e.g., petrolatum), polyhydric alcohols (e.g., propylene glycol), silicones (e.g., dimethicone), sterols (e.g., cholesterol), vegetable or animal fat (e.g., cocoa butter), vegetable wax (e.g., Carnauba wax), and wax ester (e.g., bees wax). The occlusive agent are hydrophobic agent or mixtures of hydrophobic agents that form an occlusive film on skin that reduces trans-epidermal water loss (TEWL) by preventing evaporation of water from the stratum corneum.

In an embodiment, the composition may include a stiffening agent that increases the viscosity and/or consistency of the formulation or improves the rheology of the formulation. In some embodiments, the stiffening agent component is present in an amount of about 2% to about 8% w/w. In some embodiments, the stiffening agent is selected from fatty alcohols, C12-20 fatty alcohols, cetyl alcohol and stearyl alcohol.

In some embodiments, the composition includes an emulsifier selected from glyceryl fatty esters, sorbitan fatty esters, Stearic acid 50, isopropyl myristate, glyceryl stearate, and polysorbate 20. In some embodiments, the emulsifier is present in an amount of about 0.1% to 10% w/w.

In some other embodiments, the pharmaceutical composition further comprises a stabilizing agent. In some embodiments, the stabilizing agent is present in an amount of about 0.1% to 10% w/w. In some embodiments, the stabilizing agent is selected from polysaccharides, xanthan gum and others.

In an embodiment, the skin penetration enhancer(s) includes but not limited to, Isopropyl myristate, sulphoxides such as dimethylsulphoxide (DMSO), Diethylene glycol monoethyl ether(transcutol p), azones such as laurocapram, pyrrolidones such as 2-pyrrolidone, alcohols and alkanols such as ethanol, or decanol, glycols such as propylene glycol and combinations thereof.

In an embodiment, the composition includes the skin penetration enhancer in an amount ranging from 0.01% to 10% w/w. Alternatively, the skin penetration enhancer is present in an amount ranging from 0.1% to 8% w/w.

In an embodiment, the preservative(s) includes, but are not limited to anti-microbial such as germaben II (manufactured by ICI; propylene glycol, diazolidinyl urea, methylparaben, and propylparaben), methylparaben, propylparaben, imidazolidinyl urea, benzyl alcohol, sorbic acid, benzoic acid, sodium benzoate, phenoxyethanol, dichkorobenzyl alcohol, and formaldehyde and combinations thereof. In an embodiment, the composition includes the preservative in an amount ranging from 0.1% to 15% w/w or 0.1% to 5% w/w. Alternatively, the preservative can be present in an amount ranging from 0.2% to 3% w/w.

In an embodiment, the moisturizing agent(s) includes, but are not limited to lactic acid and other hydroxy acids and their salts, glycerin, propylene glycol, butylene glycol, sodium PCA, Carbowax 200, Carbowax 400, Carbowax 800 and combinations thereof.

In an embodiment, the film former/waterproofing agent(s) includes, but are not limited to acrylates/$C_{12-22}$alkylmethacrylate copolymer, $C_{30-38}$olefin/isopropyl maleate/methylacrylate copolymer, polyethylene, waxes, vinylpyrrolidone/ dimethiconylacrylate/polycarbamyl polyglycol ester, butylated polyvinylpyrrolidone, polyvinylpyrrolidone/hexadecane copolymer, polyvinylpyrrolidone/eicosene copolymer, tricontanyl polyvinylpyrrolidone, *Brassica Campestris/ Aleuritis* Fordi Oil copolymer, aminofunctional silicones, decamethyl cyclopentasiloxane and trimethylsiloxysilicate, octadecene/methylacrylate copolymer and combinations thereof.

In an embodiment, the pH adjuster/chelating agent(s) includes, but are not limited to sodium hydroxide, triethanolamine, EDTA salt and combinations thereof.

In an embodiment, the rheology modifying agent(s) include, but are not limited to acrylates crosspolymer, acrylates/$C_{10-30}$ alkylacrylate crosspolymer, polyacrylic acid, sodium polyacrylate, polyacrylate, acrylates/vinyl ester copolymer, PVP/decene copolymer, styrene/MA copolymer, acetamide MEA, acrylamides copolymer, acrylates copolymer, acrylates/steareth-20 methacrylate copolymer, acrylates/behenyth-25 methacrylate copolymer, PEG-150/decyl alcohol/SMDI copolymer, PVP, PVM/MA decadiene crosspolymer, carbomer, PEG crosspolymer, acrylates/palmeth-25 acrylates copolymer, polysaccharide, polyether-1, sodium magnesium silicate, bentonite, trihydroxystearin, hydroxy stearate, aluminum-magnesium hydroxide stearate, acacia gum, xanthan gum, microcrystalline cellulose, cellulose gum and combinations thereof.

In an embodiment, the fragrance(s) includes, but are not limited to alcohols, aldehydes, ketones, esters, ethers, acetates, nitriles, terpene hydrocarbons, nitrogenous or sulfurous heterocyclic compounds and essential oils. However, naturally occurring plant and animal oils and exudates comprising complex mixtures of various chemical components are also known for use as "fragrance materials". The individual perfume raw materials which comprise a known natural oil can be found by reference to Journals commonly used by those skilled in the art such as "Perfume and Flavourist" or "Journal of Essential Oil Research", or those listed in reference texts such as the book by S. Arctander, Perfume and Flavor Chemicals, 1969, Montclair, N.J., USA and re-published by Allured Publishing Corporation Illinois (1994). Additionally, some perfume raw materials are supplied by the fragrance houses (Firmenich, International Flavors & Fragrances, Givaudan, Symrise) as mixtures in the form of proprietary specialty accords. Non-limiting examples of the fragrance materials useful herein include pro-fragrances such as acetal pro-fragrances, ketal pro-fragrances, ester pro-fragrances, hydrolyzable inorganicorganic pro-fragrances, and mixtures thereof. In certain embodiment the composition of the present invention can be fragrance free.

In an embodiment, the colorant(s) includes, but are not limited to FD&C Red No. 40, FD&C Yellow No. 5 and combinations thereof.

In an embodiment, the vitamin(s) includes, but are not limited to Vitamin A, C, E and combinations thereof.

While one or more embodiments of the present disclosure enumerates and describes a list of excipients that may be used in the composition to serve an intended purpose, it should be appreciated that one or more excipients may also serve more than one function, obviating the need of inclusion of separate excipients for the specified purpose. Although several embodiments of the present disclosure names few of the commonly used excipients, any other excipient known to or appreciated by a skilled person can also be used to realize the advantageous compositions of the present disclosure. Examples of useful excipients which can optionally be added to the composition are described in the Handbook of Pharmaceutical Excipients, 3rd edition, Edited by A. H. Kibbe, published by: American Pharmaceutical Association, Washington D.C., ISBN: 0-917330-96-X, and in Handbook of Pharmaceutical Excipients (4th edition), Edited by Raymond C Rowe—Publisher: Science and Practice.

The topical formulation can be prepared into various forms such as but not limited to solids, liquids, suspensions, semisolids such as creams, solution, gels, lotions, emulsion, emulsion of water and oil (oil in water or water in oil emulsion), pastes or sticks, powders and finely dispersed liquids such as sprays or mists.

In an embodiment, the composition is formulated as a topical lotion. The formulation can be applied in a wide affected area due to its low viscosity as compared with the cream formulations. Further, the advantageous lotion formulation of the present disclosure offers marked improvement in delivery of the active agent fexofenadine.

During experimentation, it could also be noted that when PEG-400 is used as one of the solvents, it results in phase separation. When propylene glycol is incorporated as part of the formulation, it could be noted, albeit surprisingly, that the problem of phase separation can be subdued. It could also be surprising to note that inclusion of benzyl alcohol in the composition dramatically inhibits formation of the RC-A impurity.

Accordingly, an aspect of the present disclosure provides a pharmaceutical composition comprising: fexofenadine or a salt or a hydrate or a solvate thereof in an amount ranging from 0.001 to 10% w/w; a diluent in an amount ranging from 30% to 80% w/w; a solvent in an amount ranging from 1% to 30% w/w; an emollient in an amount ranging from 10% to 40% w/w; a humectant in an amount ranging from 5% to 30% w/w; a preservative in an amount ranging from 0.1% to 15% w/w; an emulsifier in an amount ranging from 0.1% to 10% w/w; and a surfactant in an amount ranging from 2% to 30% w/w, said composition being formulated as a topical formulation, wherein the solvent comprises benzyl alcohol.

The compositions of the present invention may be prepared in accordance with methods well known to the person skilled in the field of pharmacy. The topical lotion formulation of the present disclosure can be prepared by the method that includes: (a) melt mixing an emollient, a humectant and a first surfactant to prepare a water immiscible phase; (b) preparing a fexofenadine solution by mixing fexofenadine or salt or solvate or hydrate thereof and optionally, a skin penetration enhancer in a solvent; (c) taking a part of water (such as 10% to 70% of the total amount of water required for preparing the formulation) and heating the water to a temperature ranging from 60° C. to 90° C.; (d) mixing a preservative and a second surfactant with the hot water to obtain a clear solution; (e) mixing the clear solution with the water immiscible phase at a temperature ranging from 60° C. to 90° C. to obtain a uniform semi-solid phase; (f) allow the semi-solid phase to cool down to a temperature less than 50° C.; (g) mixing the fexofenadine solution with the cool down semi-solid phase; (h) optionally, mixing a fragrance with the mixture from step (g); and (i) make up the weight of the formulation with water to prepare the topical lotion formulation. Similarly, the non-aqueous compositions may be prepared by incorporating the components into a well-known ointment or base excipient such as white soft paraffin (also known as vaseline, white petrolatum, Plastibase™, polyethylene, paraffin liquid, a microcrystalline wax and others. As an example, preparation of a non-aqueous composition according to the invention is typically perfumed by (i) melting the non-aqueous ingredients except drug solution into a heating vessel at about 70° C.-80° C. in vessel 1. (ii) drug solution: fexofenadine HCl is dissolved in propylene glycol and benzyl alcohol completely using magnetic stirrer (30 minutes) in separate compounding vessel. (iii) drug solution or the fexofenadine solution from step (iv) is added to the step 1 mixture once it reach a temperature of 40° C. and it is allow to mix completely to form a semi solid mixture. (v), optionally mixing a fragrance to the semi solid mixture of step (iv). The composition may also contain other commonly used additives.

Another aspect of the present disclosure relates to a method of treating an allergic condition in a patient in need thereof comprising applying to a subject a therapeutically effective amount of the pharmaceutical composition of the present disclosure.

Still another aspect of the present disclosure relates to the use of the pharmaceutical composition in the preparation of a medicament for the treatment of an allergic condition in patient in need thereof.

The compositions/formulations realized in accordance with embodiments of the present disclosure can find utility in treatment of a wide variety of allergic conditions/disorders including rashes, inflammation, urticarial flares, itching, tick bites, psoriasis, eczema and keratosis and the like conditions, which may be triggered upon a subject coming into contact with allergen(s).

Accordingly, an embodiment of the present disclosure provides a method of treatment of an allergic condition in a subject, said method comprising applying to a subject in need thereof an effective amount of a composition comprising fexofenadine or a salt or a hydrate or a solvate thereof in an amount ranging from 0.1% to 10% w/w; a diluent in an amount ranging from 30% to 80% w/w; a solvent in an amount ranging from 1% to 30% w/w; an emollient in an amount ranging from 10% to 40% w/w: a humectant in an amount ranging from 5% to 30% w/w; and a surfactant in an amount ranging from 2% to 30% w/w, said composition being formulated as a topical formulation. In an embodiment, the composition is formulated as a topical lotion. The allergic condition may be atopic contact dermatitis, rashes, inflammation, urticarial flares, urticaria, angioedema, hereditary angioedema, itching, tick bites, psoriasis, eczema, keratosis and the like conditions, which may be triggered upon a subject coming into contact with allergen(s).

Accordingly, an embodiment of the present disclosure provides a method of treatment of an allergic condition in a subject, said method comprising applying to a subject in need thereof an effective amount of a composition comprising diphenhydramine or a salt or a hydrate or a solvate thereof (for example diphenhydramine HCl) in an amount ranging from 0.1% to 10% w/w; a diluent in an amount ranging from 30% to 80% w/w; a solvent in an amount ranging from 1% to 30% w/w; an emollient in an amount ranging from 10% to 40% w/w; a humectant in an amount ranging from 5% to 30% w/w; and a surfactant in an amount ranging from 2% to 30% w/w, said composition being formulated as a topical formulation. In an embodiment, the composition is formulated as a topical lotion. The allergic condition may be rashes, inflammation, urticarial flares, itching, tick bites, psoriasis, eczema, keratosis and the like conditions, which may be triggered upon a subject coming into contact with allergen(s).

Still further embodiment of the present disclosure provides a pharmaceutical composition for use in treatment of an allergic condition, said composition comprising fexofenadine or a salt or a hydrate or a solvate thereof in an amount ranging from 0.1% to 10% w/w; a diluent in an amount ranging from 30% to 80% w/w; a solvent in an amount ranging from 1% to 30% w/w: an emollient in an amount ranging from 10% to 40% w/w: a humectant in an amount ranging from 5% to 30% w/w; and a surfactant in an amount ranging from 2% to 30% w/w, said composition being formulated as a topical formulation. The allergic condition may be rashes, inflammation, urticarial flares, itching, tick bites, psoriasis, eczema, keratosis and the like conditions, which may be triggered upon a subject coming into contact with allergen(s).

Further embodiment of the present disclosure provides a pharmaceutical composition for use in treatment of an allergic condition, said composition comprising diphenhydramine or a salt or a hydrate or a solvate thereof (for example diphenhydramine HCl) in an amount ranging from 0.1% to 10% w/w; a diluent in an amount ranging from 30% to 80% w/w; a solvent in an amount ranging from 1% to 30% w/w; an emollient in an amount ranging from 10% to 40% w/w; a humectant in an amount ranging from 5% to 30% w/w; and a surfactant in an amount ranging from 2% to 30% w/w, said composition being formulated as a topical formulation. The allergic condition may be rashes, inflammation, urticarial flares, itching, tick bites, psoriasis, eczema, keratosis and the like conditions, which may be triggered upon a subject coming into contact with allergen(s).

Yet another embodiment of the present disclosure provides use of a pharmaceutical composition for manufacture of a medicament for treatment of an allergic condition, said composition comprising fexofenadine or a sak or a hydrate or a solvate thereof in an amount ranging from 0.1% to 10% w/w: a diluent in an amount ranging from 30% to 80% w/w: a solvent in an amount ranging from 1% to 30% w/w; an emollient in an amount ranging from 10% to 40% w/w; a humectant in an amount ranging from 5% to 30% w/w; and a surfactant in an amount ranging from 2% to 30% w/w, said composition being formulated as a topical formulation. The allergic condition may be rashes, inflammation, urticarial flares, itching, tick bites, psoriasis, eczema, keratosis and the like conditions, which may be triggered upon a subject coming into contact with allergen(s).

Still yet another embodiment of the present disclosure provides use of a pharmaceutical composition for manufacture of a medicament for treatment of an allergic condition, said composition comprising diphenhydramine or a salt or a hydrate or a solvate thereof (for examples diphenhydramine HCl) in an amount ranging from 0.1% to 10% w/w; a diluent in an amount ranging from 30% to 80% w/w; a solvent in an amount ranging from 1% to 30% w/w; an emollient in an amount ranging from 10% to 40% w/w; a humectant in an amount ranging from 5% to 30% w/w; and a surfactant in an amount ranging from 2% to 30% w/w, said composition being formulated as a topical formulation. The allergic condition may be rashes, inflammation, urticarial flares, itching, tick bites, psoriasis, eczema, keratosis and the like conditions, which may be triggered upon a subject coming into contact with allergen(s).

Further embodiment of the present disclosure provides a pharmaceutical composition for treatment of an allergic condition, said composition comprising fexofenadine or a salt or a hydrate or a solvate thereof in an amount ranging from 0.1% to 10% w/w; a diluent in an amount ranging from 30% to 80% w/w; a solvent in an amount ranging from 1% to 30% w/w; an emollient in an amount ranging from 10% to 40% w/w: a humectant in an amount ranging from 5% to 30% w/w; and a surfactant in an amount ranging from 2% to 30% w/w, said composition being formulated as a topical formulation. The allergic condition may be rashes, inflammation, urticarial flares, itching, tick bites, psoriasis, eczema, keratosis and the like conditions, which may be triggered upon a subject coming into contact with allergen(s).

Further embodiment of the present disclosure provides a pharmaceutical composition for treatment of an allergic condition, said composition comprising diphenhydramine or a salt or a hydrate or a solvate thereof (for examples diphenhydramine HCl) in an amount ranging from 0.1% to 10% w/w; a diluent in an amount ranging from 30% to 80% w/w; a solvent in an amount ranging from 1% to 30% w/w; an emollient in an amount ranging from 10% to 40% w/w; a humectant in an amount ranging from 5% to 30% w/w; and a surfactant in an amount ranging from 2% to 30% w/w, said composition being formulated as a topical formulation. The allergic condition may be rashes, inflammation, urticarial flares, itching, tick bites, psoriasis, eczema, keratosis and the like conditions, which may be triggered upon a subject coming into contact with allergen(s).

Still, further embodiment of the present disclosure provides a pharmaceutical composition for treatment of psoriasis, said composition comprising fexofenadine or a salt or a hydrate or a solvate thereof in an amount ranging from 0.1% to 10% w/w; a diluent in an amount ranging from 30% to 80% w/w; a solvent in an amount ranging from 1% to 30% w/w; an emollient in an amount ranging from 10% to 40% w/w; a humectant in an amount ranging from 5% to 30% w/w; and a surfactant in an amount ranging from 2% to 30% w/w, said composition being formulated as a topical formulation.

The composition of the present disclosure affords increased therapeutic effects, and reduced adverse effects, making these pharmaceutical compositions extremely effective therapeutics, especially in the treatment of allergic diseases/conditions. Therapeutic levels of the formulation will vary with the progression stage of disease/allergic condition. The formulation in the appropriate amounts and intervals effective to treat skin allergic conditions such as rashes, inflammation, urticarial flares, itching, tick bites, psoriasis, eczema, keratosis and the like conditions, which may be triggered upon a subject coming into contact with allergen(s).

The compositions of the present disclosure is a non-sedating composition. The topical composition increases the neovascularization, fibroblast proliferation, pepsin-soluble collagen synthesis, stabilizes mast cells and increases the turnover of collagen in wounds. It enhances the permeability barrier homeostasis in normal skin, enhance corneocyte envelope thickness, and stimulate epidermal differentiation and epidermal lipid synthesis. It reduces body's reaction to an allergen and decrease itching and irritation and forms a layer of hydration on top of the skin, providing softness and smoothness.

The composition of the present disclosure may further be combined with one or more other active agents as described in the disclosure to effectively inhibit microbial growth, reduced inflammation, hastens wound healing, reduces allergen induced inflammation, improve the skin hydration and provides relief from the allergic conditions in short time. This composition effectively controls the symptoms without having to take multiple drugs.

Further this composition relieves symptoms in individuals with mastocytosis or to prevent and relieve itchy local allergic reactions to insect bites Further, the patient may apply the formulation once a day, twice a day or thrice a day, for a period of 5 days to a month or even up to two months, three months, four months, five months and six months, as advised by the medical practitioner/experts, depending upon the severity of the skin allergic condition.

In an embodiment, the disclosure provides a method for treating allergic diseases/conditions, said method includes providing a container that is suitable for storing the topical formulation for pharmaceutical use, the container comprising an applicator that is capable of dispensing a pharmaceutically effective dose of an fexofenadine topical formulation and spreading an approximately uniform amount of the topical formulation on a target area; loading the applicator with the dose of the topical formulation, and administering the dose of the topical formulation to the treatment area by uniform manual spreading. In some embodiment, the container is a squeeze sensitive container, and the applicator is a flow through applicator which delivers the topical formulation to the target area when a user applies sufficient pressure on the container.

In another embodiment, the topical formulation is delivered using a transdermal delivery system designed to deliver the fexofenadine composition to the skin and into systemic circulation. The transdermal delivery system includes matrix type, liquid or gel reservoir type delivery systems. In some embodiments, topical delivery systems are designed to deliver the active ingredient to local tissue.

Non-limiting examples of transdermal delivery systems include: iontophoresis, voltage-gradient iontophoresis, electroporation, sonophoresis, magnetophoresis, dermal patches (vapor patches, adhesive patches), nanocarriers, needled and needle-less shots, microneedles, thermal ablation, microdermabrasion, electroporation, radiofrequency usage, microporation, use of thermal techniques, micro and radio waves, electro-mechanical devices, nano deliveries and cavitational ultrasound techniques and injectors such as jet injectors, powderject, Implaject®, Crossjet®, Imitrex® and likes. Transdermal delivery systems deliver the active ingredient in a discrete dosage form from a skin-sticker patch or other transdermal methods/device by crossing through the skin layers to the systemic circulation. TDDS patches can be a single- and multiple-layered devices, vapor patches, drug and polymer matrix characteristic-based products, as well as reservoir-based delivery systems. The patches may include polymeric membrane to control the drug release rate, which depends on the polymer properties, permeability coefficient, membrane thickness and the adhesive. The adhesive-dispersion type TDDS/devices uses polymer, such as polyisobutylene or polyacrylate, as the adhesive polymer with specific permeability thus controls the drug diffusion rate.

In some embodiments, the topical composition is a transdermal patch filled with the precise fexofenadine dose and stuck to the skin for easy delivery of the drug into the blood circulation with help from enhancers. In certain aspects, suitable polymers, permeation enhancers and solvents are employed. Examples include chitosan, a polysaccharide, hyaluronic acid, synthetic polymer-bused hydrogels are prepared from polyacrylics and polyacrylamide. Poly(2-hydroxyethyl methacrylate (p-HEMA), methyl methacrylate copolymers (Eudragit®), poly-N-vinylamide, povidone, and ±lactic acid oligomers (DLLO), polyurethanes (PUs), polyurethane elastomer hydrogels, acrylates, silicones, polyisobutylenes, Polyvinyl alcohol (PVA), hydroxypropyl methylcellulose (HPMC), polyacrylics, Trihydroxy bile salts, monosodium glycolate, taurocholate sodium, dihydroxy salts, deoxycholate sodium, sodium glyco-deoxycholate and sodium taurodeoxycholate are also used as permeation enhancers. Binary system-based fatty acids, i.e. propylene glycol-oleic acid and 1,4-butane diol-linoleic acid, N,N-dimethyl-m-toluamide, calcium thioglycolate, eucalyptol, di-o-methyl-β-cyclodextrin, sodium caprylate mixed with glyceryl triglyceride, short chain glyceryl monocaprylate, imidic cyclic urea, cyclopentadecalactone, cyclodextrins, and the likes.

In certain embodiments, the microneedles are used in combination with sonophoresis electroporation, iontophoresis to control the drug release rate and to provide improved delivery.

NON-LIMITING EXEMPLARY COMPOSITIONS

Batch ACG001C0140040
Topical lotion formulation was prepared using the composition as provided in Table 1 below

TABLE 1

Composition comprising fexofenadine for topical application

| S. No. | Ingredients | % (w/w) |
|---|---|---|
| 1 | Fexofenadine HCl | 1.0% |
| 2 | Propylene glycol | 10.0% |
| 3 | Transcutol P | 5.0% |
| 4 | White Petrolatum | 5.0% |
| 5 | Light Mineral oil | 6.0% |
| 6 | Isopropyl Myristate | 5.0% |
| 7 | Glycerin | 5.0% |
| 8 | Cetyl alcohol | 1.0% |
| 9 | Polysorbate 60 | 2.5% |
| 10 | Span 60 | 2.5% |
| 11 | Stearic acid 50 | 1.0% |
| 12 | Methyl Paraben | 0.1% |
| 13 | Propyl Paraben | 0.1% |
| 14 | Lemon oil natural | 0.1% |
| 15 | Water | QS to 100% |

Methods of Preparation of Topical Lotion Formulation of Fexofenadine:
Step 1: White petrolatum, light mineral oil, isopropyl myristate, Span 60, cetyl alcohol, and stearic acid 50 were charged into a heating vessel 1 and heated to about 70° C. to 80° C. to dissolve all the excipients to obtain a water immiscible phase.
Step 2: Preparation of Fexofenadine HCl solution; Propylene glycol and Transcutol P were taken in compounding vessel 2 and fexofenadine HCl is added into it, and stirred using magnetic stirrer for about 20 minutes till the Fexofenadine HCl is completely dissolved. Similarly, other H1 antagonist solution can also prepared by replacing the active agent of step 2.

Step 3: 50% batch quantity of water is taken into a heating vessel 3 and heated to 70° C. to 80° C. and then methyl paraben, propyl paraben, glycerol, polysorbate 60 were added into it and stirred for about 30 minutes using magnetic stirrer till a clear solution was obtained.

Step 4: The clear solution obtained in step 3 is added into the heating vessel 1 containing the water immiscible phase obtained from step 1 at a temperature about 70° C.-80° C. and mixed thoroughly to obtain a uniform semi-solid phase.

Step 5: The temperature of the semi-solid phase of step 4 in the heating vessel 1 is allowed to reach 40° C. (room temperature) slowly and then Fexofenadine HCl solution obtained from step 2 is added and mixed completely.

Step 6: Lemon oil natural is added into the semisolid mixture of step 5.

Step 7: Final weight of the composition is adjusted with water to 100%.

BATCH ACG001C0140045

Topical lotion formulation was prepared using the composition as provided in Table 2 below.

TABLE 2

Composition comprising fexofenadine for topical application

| S. No. | Ingredients | % (w/w) |
|---|---|---|
| 1 | Fexofenadine HCl | 1.0% |
| 2 | Propylene glycol | 10.0% |
| 3 | Transcutol P | 5.0% |
| 4 | Benzyl alcohol | 2.0% |
| 5 | White Petrolatum | 5.0% |
| 6 | Light Mineral oil | 6.0% |
| 7 | Isopropyl Myristate | 5.0% |
| 8 | Glycerol | 5.0% |
| 9 | Cetyl alcohol | 1.0% |
| 10 | Polysorbate 60 | 2.5% |
| 11 | Span 60 | 2.5% |
| 12 | Stearic acid 50 | 1.0% |
| 13 | Lemon oil natural | 0.1% |
| 14 | Water | QS to 100% |

Method of Preparation of Topical Lotion Formulation of Fexofenadine:

Step 1: White petrolatum, light mineral oil, isopropyl myristate, Span 60, cetyl alcohol, and stearic acid 50 were charged into a heating vessel 1 and heated up to 70° C. to 80° C. to dissolve all the excipients to obtain a water immiscible phase.

Step 2: Preparation of Fexofenadine HCl solution: Propylene glycol, benzyl alcohol and Transcutol P were taken in compounding vessel 2 and Fexofenadine HCl is added and stirred using a magnetic stirrer for about 20 minutes till the Fexofenadine HCl is completely dissolved.

Step 3: 50% batch quantity of water is taken into a heating vessel 3 and heated to 70° C. to 80° C. and then glycerol and polysorbate 60 is added and stirred for about 30 minutes using magnetic stirrer till a clear solution is obtained.

Step 4: The clear solution obtained in Step 3 is added into the water immiscible phase in heating vessel 1 of step 1 at 70° C.-80° C. and mixed thoroughly to obtain a uniform semi-solid phase.

Step 5: The temperature of the semi-solid phase of step 4 in the heating vessel 1 is allowed to reach 40° C. (room temperature) slowly and then fexofenadine HCl solution obtained from step 2 is added into it and mixed completely.

Step 6: Lemon oil natural is added into the above semisolid phase obtained from step 5.

Step 7: Final weight of the composition is adjusted with water to 100%.

BATCH ACG001C0140001

Topical lotion formulation was prepared using the composition as provided in Table 3 below. Topical lotion formulation was prepared following the same method as described in above example (for batch ACG001C0140040).

TABLE 3

Composition comprising fexofenadine for topical application ACG001C0140001

| S. No. | Ingredients | % (w/w) |
|---|---|---|
| 1 | Fexofenadine HCl | 1.0% |
| 2 | DGLF | 0.1% |
| 3 | Propylene glycol | 10.0% |
| 4 | isopropyl alcohol | 5.0% |
| 5 | White Petrolatum | 5.0% |
| 6 | Light Mineral oil | 6.0% |
| 7 | Isopropyl Myristate | 5.0% |
| 8 | Glycerol | 5.0% |
| 9 | Glyceryl monostearate 40 | 1.5% |
| 10 | Cetyl alcohol | 1.0% |
| 11 | Stearic acid 50 | 5.0% |
| 12 | Polysorbate 60 | 8.0% |
| 13 | Water | QS to 100% |

TABLE 4

Stability results of ACG001C0140001

| Batch No. | Description | pH | Label claim Fexo (%) | Assay % HCl | Assay % DGLF | RCB | RRT 1.63 RCA | RRT 1.80 RCA | RRT 3.28 DCB | RRT 3.78 | % Total |
|---|---|---|---|---|---|---|---|---|---|---|---|
| ACG001C0140001 | white color cream | NA | 1.07 | 107.0 | 98.1 | NA | 0.01 | 0.01 | BDL | BDL | 0.02 |

BATCH ACG001C0140002

Topical lotion formulation was prepared using the composition as provided in Table 5 below. Topical lotion formulation was prepared following the same method as described in above example (for batch ACG001C0140040).

TABLE 5

Composition comprising fexofenadine for topical application

| S. No. | Ingredients | % (w/w) |
|---|---|---|
| 1 | Fexofenadine HCl | 1.0% |
| 2 | DGLF | 0.1% |
| 3 | Propylene glycol | 10.0% |
| 4 | Isopropyl alcohol | 5.0% |
| 5 | White Petrolatum | 5.0% |
| 6 | Light Mineral oil | 6.0% |
| 7 | Isopropyl Myristate | 5.0% |
| 8 | Glycerol | 5.0% |
| 9 | Glyceryl monostearate 40 | 1.5% |
| 10 | Cetyl alcohol | 1.0% |
| 11 | Stearic acid 50 | 3.0% |
| 12 | Polysorbate 60 | 8.0% |
| 13 | Water | QS to 100% |

BATCH ACG001C0140003

Topical lotion formulation was prepared using the composition as provided in Table 6 below. Topical lotion formulation was prepared following the same method as described in above example (for batch ACG001C0140040).

TABLE 6

Composition comprising fexofenadine for topical application

| S. No. | Ingredients | % (w/w) |
|---|---|---|
| 1 | Fexofenadine HCl | 1.0% |
| 2 | DGLF | 0.1% |
| 3 | Propylene glycol | 10.0% |
| 4 | Isopropyl alcohol | 5.0% |
| 5 | White Petrolatum | 5.0% |
| 6 | Light Mineral oil | 6.0% |
| 7 | Isopropyl Myristate | 5.0% |
| 8 | Glycerol | 5.0% |
| 9 | Glyceryl monostearate 40 | 1.5% |
| 10 | Cetyl alcohol | 1.0% |
| 11 | Stearic acid 50 | 3.0% |
| 12 | Polysorbate 60 | 5.0% |
| 13 | Water | QS to 100% |

BATCH ACG001C0140004

Topical lotion formulation was prepared using the composition as provided in Table 7 below. Topical lotion formulation was prepared following the same method as described in above example (for batch ACG001C0140040).

TABLE 7

Composition comprising fexofenadine for topical application

| S. No. | Ingredients | % (w/w) |
|---|---|---|
| 1 | Fexofenadine HCl | 1.0% |
| 2 | DGLF | 0.1% |
| 3 | Propylene glycol | 10.0% |
| 4 | Isopropyl alcohol | 5.0% |
| 5 | White Petrolatum | 5.0% |
| 6 | Light Mineral oil | 6.0% |
| 7 | Isopropyl Myristate | 5.0% |
| 8 | Glycerol | 5.0% |
| 9 | Glyceryl monostearate 40 | 1.5% |

TABLE 7-continued

Composition comprising fexofenadine for topical application

| S. No. | Ingredients | % (w/w) |
|---|---|---|
| 10 | Cetyl alcohol | 1.0% |
| 11 | Stearic acid 50 | 3.0% |
| 12 | Polysorbate 60 | 6.6% |
| 13 | Water | QS to 100% |

BATCH ACG001C0140005

Topical lotion formulation was prepared using the composition as provided in Table 9 below. Topical lotion formulation was prepared following the same method as described in above example (for batch ACG001C0140040).

TABLE 9

Composition comprising fexofenadine for topical application

| S. No. | Ingredients | % (w/w) |
|---|---|---|
| 1 | Fexofenadine HCl | 1.0% |
| 2 | DGLF | 0.1% |
| 3 | Propylene glycol | 10.0% |
| 4 | Isopropyl alcohol | 5.0% |
| 5 | White Petrolatum | 5.0% |
| 6 | Light Mineral oil | 6.0% |
| 7 | Isopropyl Myristate | 5.0% |
| 8 | Glycerol | 5.0% |
| 9 | Glyceryl monostearate 40 | 1.5% |
| 10 | Cetyl alcohol | 1.0% |
| 11 | Stearic acid 50 | 3.0% |
| 12 | Macrogol cetostearyl ether 12 | 5.0% |
| 13 | Water | QS to 100% |

BATCH ACG001C0140009

Topical lotion formulation was prepared using the composition as provided in Table 11 below. Topical lotion formulation was prepared following the same method as described in above example (for batch ACG001C0140040).

TABLE 9

Composition comprising fexofenadine for topical application

| S. No. | Ingredients | % (w/w) |
|---|---|---|
| 1 | Fexofenadine HCl | 1.0% |
| 2 | DGLF | 0.1% |
| 3 | Propylene glycol | 10.0% |
| 4 | Isopropyl alcohol | 5.0% |
| 5 | White Petrolatum | 5.0% |
| 6 | Light Mineral oil | 6.0% |
| 7 | Isopropyl Myristate | 5.0% |
| 8 | Glycerol | 5.0% |
| 9 | Glyceryl monostearate 40 | 1.5% |
| 10 | Cetyl alcohol | 1.0% |
| 11 | Polysorbate 60 | 6.6% |
| 12 | Stearic acid 50 | 1.0% |
| 13 | Methyl Paraben | 0.1% |
| 14 | Propyl Paraben | 0.1% |
| 15 | Water | QS to 100% |

TABLE 10

Stability results of ACG001C0140009

| Batch No. | Description | Labelled amount of Fexo | Assay % Fexo HCl | Assay % DGLF | RCB | RRT 1.63 | RRT 1.80 RCA | RRT 3.28 DCB | RRT 3.78 | % Total |
|---|---|---|---|---|---|---|---|---|---|---|
| ACG001C0140000 | off white colour | 1.87 | 186.7 | 212.2 | NA | 0.02 | 0.04 | 0.02 | 0.07 | 0.15 |

BATCH ACG001C0140012

Topical lotion formulation was prepared using the composition as provided in Table 13 below. Topical lotion formulation was prepared following the same method as described in above example (for batch ACG001C0140040).

TABLE 11

Composition comprising fexofenadine for topical application

| S. No. | Ingredients | % (w/w) |
|---|---|---|
| 1 | Fexofenadine HCL | 1.0% |
| 2 | DGLF | 0.1% |
| 3 | Propylene glycol | 10.0% |
| 4 | Transcutol-P | 5.0% |
| 5 | White Petrolatum | 5.0% |
| 6 | Light Mineral oil | 6.0% |
| 7 | Isopropyl Myristate | 5.0% |
| 8 | Glycerol | 5.0% |
| 9 | Glyceryl monostearate 40 | 1.5% |
| 10 | Cetyl alcohol | 1.0% |
| 11 | Polysorbate 60 | 6.6% |
| 12 | Stearic acid 50 | 1.0% |
| 13 | Methyl Paraben | 0.1% |
| 14 | Propyl Paraben | 0.1% |
| 15 | Water | QS to 100% |

TABLE 12

Stability results of ACG001C0140012

| Batch No. | Description | LC of Fexo % w/w | Assay % Fexo HCl | Assay % DGLF | RCB | RRT 1.63 | RRT 1.80 RCA | RRT 3.28 DCB | RRT 3.78 | % Total |
|---|---|---|---|---|---|---|---|---|---|---|
| ACG001C0140012 | white colour lotion | 1.09 | 109.5 | N/A | NT | 0.02 | BDL | 0.03 | 0.02 | 0.07 |

BATCH ACG001C0140018

Topical lotion formulation was prepared using the composition as provided in Table 15 below. Topical lotion formulation was prepared following the same method as described in above example (for batch ACG001C0140040).

TABLE 13

Composition comprising fexofenadine for topical application

| S. No. | Ingredients | % (w/w) |
|---|---|---|
| 1 | Fexofenadine HCL | 1.0% |
| 2 | PEG 400 | 5.0% |
| 3 | Benzyl Alcohol | 2.0% |
| 4 | Transcutol-P | 5.0% |
| 5 | White Petrolatum | 5.0% |
| 6 | Light Mineral oil | 6.0% |
| 7 | Isopropyl Myristate | 5.0% |
| 8 | Glycerol | 5.0% |
| 9 | Glyceryl monostearate 40 | 1.5% |
| 10 | Cetyl alcohol | 1.0% |
| 11 | Polysorbate 60 | 6.6% |
| 12 | Stearic acid 50 | 1.0% |
| 13 | Water | QS to 100% |

BATCH ACG001C0140019

Topical lotion formulation was prepared using the composition as provided in Table 16 below. Topical lotion formulation was prepared following the same method as described in above example (for batch ACG001C0140040).

TABLE 14

Composition comprising fexofenadine for topical application

| S. No. | Ingredients | % (w/w) |
|---|---|---|
| 1 | Fexofenadine HCL | 1.0% |
| 2 | PEG 400 | 5.0% |
| 3 | Benzyl Alcohol | 2.0% |
| 4 | Transcutol-P | 5.0% |
| 5 | White Petrolatum | 5.0% |
| 6 | Light Mineral oil | 6.0% |
| 7 | Isopropyl Myristate | 5.0% |
| 8 | Glycerin | 5.0% |
| 9 | Glyceryl monostearate 40 | 1.5% |
| 10 | Cetyl alcohol | 1.0% |
| 11 | Cremophor EL | 4.0% |
| 12 | Stearic acid 50 | 1.0% |
| 13 | Water | QS to 100% |

BATCH ACG001C0140020

Topical lotion formulation was prepared using the composition as provided in Table 17 below. Topical lotion formulation was prepared following the same method as described in above example (for batch ACG001C0140040).

TABLE 15

Composition comprising fexofenadine for topical application

| S. No. | Ingredients | % (w/w) |
| --- | --- | --- |
| 1 | Fexofenadine HCL | 1.0% |
| 2 | DGLF | 0.1% |
| 3 | Propylene glycol | 10.0% |
| 4 | Transcutol-P | 5.0% |
| 5 | White Petrolatum | 5.0% |
| 6 | Light Mineral oil | 6.0% |
| 7 | Isopropyl Myristate | 5.0% |
| 8 | Glycerol | 5.0% |
| 9 | Glyceryl monostearate 40 | 1.5% |
| 10 | Cetyl alcohol | 1.0% |
| 11 | Polysorbate 60 | 6.6% |
| 12 | Stearic acid 50 | 1.0% |
| 13 | Methyl Paraben | 0.1% |
| 14 | Propyl Paraben | 0.1% |
| 15 | Water | QS to 100% |

BATCH ACG001C0140023

Topical lotion formulation was prepared using the composition as provided in Table 18 below. Topical lotion formulation was prepared following the same method as described in above example (for batch ACG001C0140040).

TABLE 16

Composition comprising fexofenadine for topical application

| S. No. | Ingredients | % (w/w) |
| --- | --- | --- |
| 1 | Fexofenadine HCL | 0.5% |
| 2 | PEG 400 | 5.0% |
| 3 | Benzyl Alcohol | 2.0% |
| 4 | Transcutol-P | 5.0% |
| 5 | Isopropyl Myristate | 5.0% |
| 6 | Glycerol | 5.0% |
| 7 | Glyceryl monostearate 40 | 1.5% |
| 8 | Cetyl alcohol | 1.0% |
| 9 | Stearic acid 50 | 1.0% |
| 10 | Gellucire 44/14 | 7.5% |
| 11 | Water | QS to 100% |

BATCH ACG001C0140024

Topical lotion formulation was prepared using the composition as provided in Table 19 below. Topical lotion formulation was prepared following the same method as described in above example (for batch ACG001C0140040).

TABLE 17

Composition comprising fexofenadine for topical application

| S. No. | Ingredients | % (w/w) |
| --- | --- | --- |
| 1 | Fexofenadine HCL | 0.5% |
| 2 | Propylene glycol | 5.0% |
| 3 | Benzyl Alcohol | 2.0% |
| 4 | Transcutol-P | 5.0% |
| 5 | Isopropyl Myristate | 5.0% |
| 6 | Glycerol | 5.0% |
| 7 | Glyceryl monostearate 40 | 1.5% |
| 8 | Cetyl alcohol | 1.0% |
| 9 | Stearic acid 50 | 1.0% |
| 10 | Gellucire 44/14 | 7.5% |
| 11 | Water | QS to 100% |

BATCH ACG001C0140025

Topical lotion formulation was prepared using the composition as provided in Table 20 below. Topical lotion formulation was prepared following the same method as described in above example (for batch ACG001C0140040).

TABLE 18

Composition comprising fexofenadine for topical application

| S. No. | Ingredients | % (w/w) |
| --- | --- | --- |
| 1 | Fexofenadine HCL | 0.5% |
| 2 | Benzyl Alcohol | 2.0% |
| 3 | Transcutol-P | 5.0% |
| 4 | Isopropyl Myristate | 5.0% |
| 5 | Glycerin | 5.0% |
| 6 | Glyceryl monostearate 40 | 1.5% |
| 7 | Cetyl alcohol | 1.0% |
| 8 | Stearic acid 50 | 1.0% |
| 9 | Gellucire 44/14 | 7.5% |
| 10 | Water | QS to 100% |

BATCH ACG001C0140026

Topical lotion formulation was prepared using the composition as provided in Table 21 and 21 A below.

TABLE 19

Composition comprising fexofenadine for topical application

| S. No. | Ingredients | % (w/w) |
| --- | --- | --- |
| 1 | Fexofenadine HCL | 0.5% |
| 2 | Propylene glycol | 10.0% |
| 3 | Benzyl Alcohol | 2.0% |
| 4 | White Petrolatum | 5.0% |
| 5 | Light Mineral oil | 6.0% |
| 6 | Cetostearyl alcohol | 7.0% |
| 7 | Ceteareth 20 | 2.2% |
| 8 | Water | QS to 100% |

TABLE 20

Composition comprising fexofenadine HCl ACG001C0140051

| Ingredients | % (w/w) |
| --- | --- |
| Fexofenadine HCL | 1.0 |
| Propylene glycol | 10.0 |
| Benzyl Alcohol | 2.0 |
| White Petrolatum | 5.0 |
| Light Mineral oil | 6.0 |
| Cetostearyl alcohol | 7.0 |
| Ceteareth 20 | 2.2 |
| Lemon oil natural | 0.1 |
| Purified Water | QS to 100 |

TABLE 21

Stability test results

| Batch No. | Condition | % Assay | RRT 0.41 | RRT 0.54 | RRT 0.66 | RRT 0.88 | RRT 1.19 | RRT 1.31 | RRT 1.44 | RRT 1.64 | RCA |
|---|---|---|---|---|---|---|---|---|---|---|---|
| ACG001C0140025 | Initial | 101.7 | ND | ND | ND | ND | ND | ND | ND | 0.01 | 0.06 |
| ACG0O1C0140926 | Initial | 101.1 | 0.01 | 0.07 | ND | ND | ND | ND | ND | 0.01 | 0.01 |
| ACG001C0140004 | 25° C.-3M | 90.0 | ND | 0.01 | ND | 0.02 | 0.03 | 0.05 | ND | 0.20 | 0.16 |
| ACG001C0140004 | 30° C.-3M | 99.3 | 0.01 | 0.01 | ND | 0.02 | 0.04 | 0.07 | 0.09 | 0.20 | 0.34 |
| ACG001C0140004 | 40° C.-3M | 97.2 | 0.011 | 0.033 | 0.02 | 0.01 | 0.03 | 0.03 | 0.05 | N | 1.26 |

| Batch No. | RRT 1.72 | RRT 2.27 | RRT 2.31 | RRT 2.39 | RRT 2.73 | RRT 3.46 | RRT 3.92 | Total |
|---|---|---|---|---|---|---|---|---|
| ACG001C0140025 | ND | ND | ND | ND | ND | ND | ND | 0.07 |
| ACG0O1C0140926 | ND | ND | ND | ND | ND | 0.03 | 0.03 | 0.18 |
| ACG001C0140004 | ND | 0.01 | 0.02 | 0.02 | 0.08 | 0.02 | 0.04 | 0.66 |
| ACG001C0140004 | 0.07 | ND | ND | 0.02 | ND | 0.02 | 0.04 | 1.05 |
| ACG001C0140004 | ND | ND | ND | ND | 0.01 | 0.10 | 0.05 | 1.60 |

Manufacturing Procedure:

Step 1: Charge all ingredients except drug solution in the heating vessel 1 and heat to 70° C.-80° C. to melt the ingredients.

Step 2: Prepare drug phase by dissolving fexofenadine HCl completely into propylene glycol and benzyl alcohol in compounding vessel 2 using magnetic stirrer for 30 minutes.

Step 3: The temperature of the heating vessel 1, is allowed to reach 40° C. slowly and then add drug phase obtained from step 2 into heating vessel 1 and allow to mix completely.

Step 4: Add Lemon oil natural to the semisolid mix obtained at step 3.

Step 5: Final weight of the composition is adjusted with water to 100%.

BATCH ACG001C0140032

Topical lotion formulation was prepared using the composition as provided in Table 23 below. Topical lotion formulation was prepared following the same method as described in above example (for batch ACG001C0140040).

TABLE 22

Composition comprising fexofenadine for topical application

| S. No. | Ingredients | % (w/w) |
|---|---|---|
| 1 | Fexofenadine HCL | 0.5% |
| 2 | Propylene glycol | 10.0% |
| 3 | Benzyl Alcohol | 2.0% |
| 4 | White Petrolatum | 5.0% |
| 5 | Light Mineral oil | 6.0% |
| 6 | Cetostearyl alcohol | 7.0% |
| 7 | Ceteareth 20 | 2.2% |
| 8 | 1N NaOH | QS to pH 6.5 |
| 9 | Purified Water | QS to 100% |

BATCH ACG001C0140033

Topical lotion formulation was prepared using the composition as provided in Table 24 below. Topical lotion formulation was prepared following the same method as described in above example (for batch ACG001C0140040).

TABLE 23

Composition comprising fexofenadine for topical application

| S. No. | Ingredients | % (w/w) |
|---|---|---|
| 1 | Fexofenadine HCL | 1.0% |
| 2 | Propylene glycol | 10.0% |
| 3 | Isopropyl alcohol | 5.0% |
| 4 | White Petrolatum | 5.0% |
| 5 | Light Mineral oil | 6.0% |
| 6 | Isopropyl Myristate | 5.0% |
| 7 | Glycerol | 5.0% |
| 8 | Glyceryl monostearate 40 | 1.5% |
| 9 | Cetyl alcohol | 1.0% |
| 10 | Stearic acid 50 | 3.0% |
| 11 | Polysorbate 60 | 6.6% |
| 12 | IN NaOH | QS to pH 6.5 |
| 13 | Purified Water | QS to 100% |

BATCH ACG001C0140036

Topical lotion formulation was prepared using the composition as provided in Table 25 below. Topical lotion formulation was prepared following the same method as described in above example (for batch ACG001C0140040).

TABLE 24

Composition comprising fexofenadine for topical application

| S. No. | Ingredients | % (w/w) |
|---|---|---|
| 1 | Fexofenadine | 1.0% |
| 2 | Propylene glycol | 10.0% |
| 3 | Transcutol P | 5.0% |
| 4 | White Petrolatum | 5.0% |
| 5 | Light Mineral oil | 6.0% |
| 6 | Isopropyl Myristate | 5.0% |
| 7 | Glycerol | 5.0% |
| 8 | Cetyl alcohol | 1.0% |
| 9 | Polysorbate 60 | 2.5% |
| 10 | Span 60 | 2.5% |
| 11 | Stearic acid 50 | 1.0% |
| 12 | Methyl Paraben | 0.1% |
| 13 | Propyl Paraben | 0.1% |
| 14 | Water | QS to 100% |

BATCH ACG001C0140039

Topical lotion formulation was prepared using the composition as provided in Table 25 below. Topical lotion formulation was prepared following the same method as described in above example (for batch ACG001C0140040).

TABLE 25

Composition comprising fexofenadine for topical application

| S. No. | Ingredients | % (w/w) | Quality Reference | Function |
|---|---|---|---|---|
| 1 | Fexofenadine HCL | 0.5% | USP | API |
| 2 | Propylene glycol | 10.0% | USP | Solvent/Co-solvent |
| 3 | Benzyl Alcohol | 2.0% | USP | Preservative |
| 4 | White Petrolatum | 5.0% | USP | Emollient |
| 5 | Light Mineral oil | 6.0% | USP | Emollient |
| 6 | Cetostearyl alcohol | 7.0% | USP | Emulsion stabilizer |
| 7 | Polyoxyl 20 cetostearyl ether (Ceteareth 20) | 2.2% | USP | Emulsifier |
| 8 | Lemon oil natural | 0.1% | USP | Fragrance |
| 9 | Purified Water | QS to 100% | Millipore | Diluent |

Characterization data for BATCH ACG001C0140039 pH: A sample of 1 g is added to a test tube and 9 ml of deionized water is added. After 10 min on a vortex the mixture is filtrated. The lotion is heated to 50° C. for 15 min to melt the lipids. Then mixed using vortex again for 10 min and filtrated. The pH is measured in triplicate experiments using pH-meter. The pH of the present formulation is found to be 4.0±0.2

Density: The density of the lotion is measured psychometrically and the value is found to be 0.95 g/cm$^3$ Texture analysis: Texture is analyzed using Stable Microsystems. TTC spreadability RIG cone is used as probe to measure the firmness and consistency of the formulation. It comprises of a male 90° cone probe and product holder. The material is deposited in the lower cone (product holder) in advance of testing and then the surface is levelled. The sample holder is stored in ambient environments before testing of the sample. The container is positioned centrally 23 mm below the probe and it is held to prevent it from lifting during probe return. Texture analyses are performed in triplicate measurements. Below given parameters are set for measuring the sample characteristics. The results are given in FIG. 1 and Table 27 and 28.

TABLE 26

Parameters set for Texture analysis
Settings & Parameters

| | |
|---|---|
| Pre-Test Speed | 1.00 mm/sec |
| Test Speed | 3.00 mm/sec |
| Post-Test Speed | 10.00 mm/sec |
| Target Mode | Distance |
| Force | 100.0 g |
| Distance | 23.000 mm |
| Strain | 10.0% |
| Trigger Force | 5.0 g |
| Probe | HDP/SR; Spreadability RIG |

TABLE 27

Texture profile of cream

| | Firmness [g] | Consistency [s] |
|---|---|---|
| ACG001C0140039 | 181.216 ± 4.2 | 156.546 ± 2.6 |

Peak (maximum force) is considered a measure of firmness—the bigger the force the thicker is the sample. The area under the upper curve is a measure of consistency—the higher the value the thicker consistency of the sample. The negative part of the curve is produced on probe return. The maximum negative force is considered an indication of cohesiveness. The bigger the force the more cohesive is the sample. The higher value the negative area, the more resistant to withdrawal of the sample. This is considered as index of viscosity of the sample. The observed firmness and consistency values are comparable with the lotions available in the market.

Figure 2:
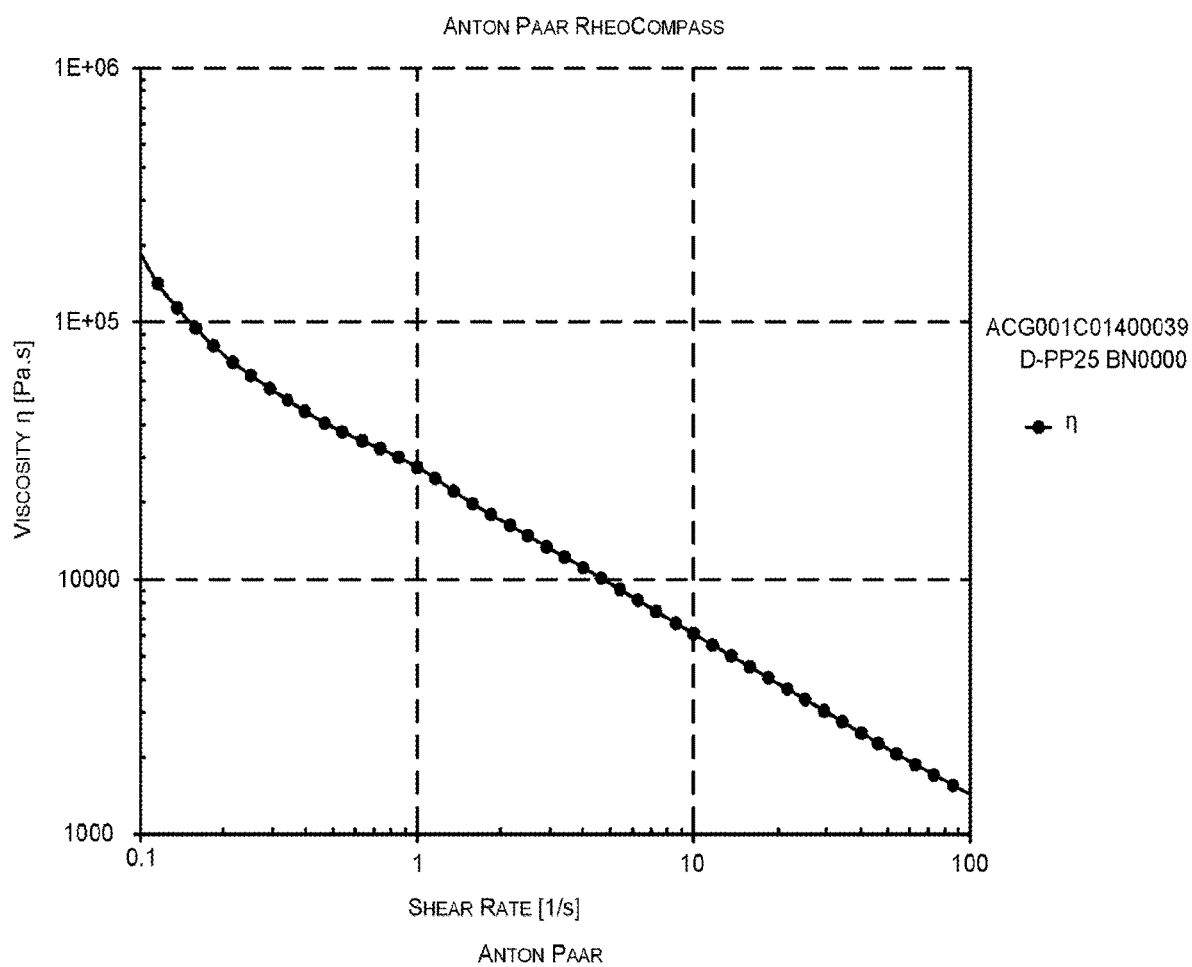
FIG. 2: Rheogram of batch ACG001C0140039

Rheology of the composition Is measured using Anton paar, parallel-plate systems that contains fixed plate and the rotating bob. The bob is shaped as a plate. Due to the narrow gaps, only a small amount of sample is required. The sample is deposited on a plate and sample viscosity is measured between shear rate 0-100 1/s, data is analyzed using Rheocompass software. The results are given in FIG. 2 & Table 29.

TABLE 28

Viscosity values at different shear rates and shear stress

| Shear rate [1/s] | Shear Stress τ (tau) | Viscosity η [Pa · s] |
|---|---|---|
| 0.1 | 18.552 | 1.8556E+05 |
| 10 | 60.836 | 6083.6 |
| 100 | | 1800.3 |

Majority of dermatological formulations show shear thinning behavior; therefore the applied shear rate significantly affects resulting shear viscosities. When shear thinning occurs, measurements at one shear rate are not recommended. Within the slope of the viscosity curve varying results can be obtained and formulations might show varying slopes. At very low shear rates, the viscosity might reach a plateau, the so called zero shear viscosity. This is relevant for storage stability and diffusion/penetration of APIs. The medium shear viscosity represents pumping processes or the spreading of the formulation. High shear viscosity might be reached at high shear rates (>100 1/s) as the formulation flows and might be broken down. This is relevant for its spreading behavior. It is inferred that the formulation shown no resistance even at lowest shear rates. This is most desirable to the lotions and creams as it improves the ease of application. The formulation has not shown any lag in change of viscosity even at lowest shear rates assuring its application over wide range of skin.

In-Vitro Drug Release Test (IVRT) (ACG001C0140039)

Figure 3:
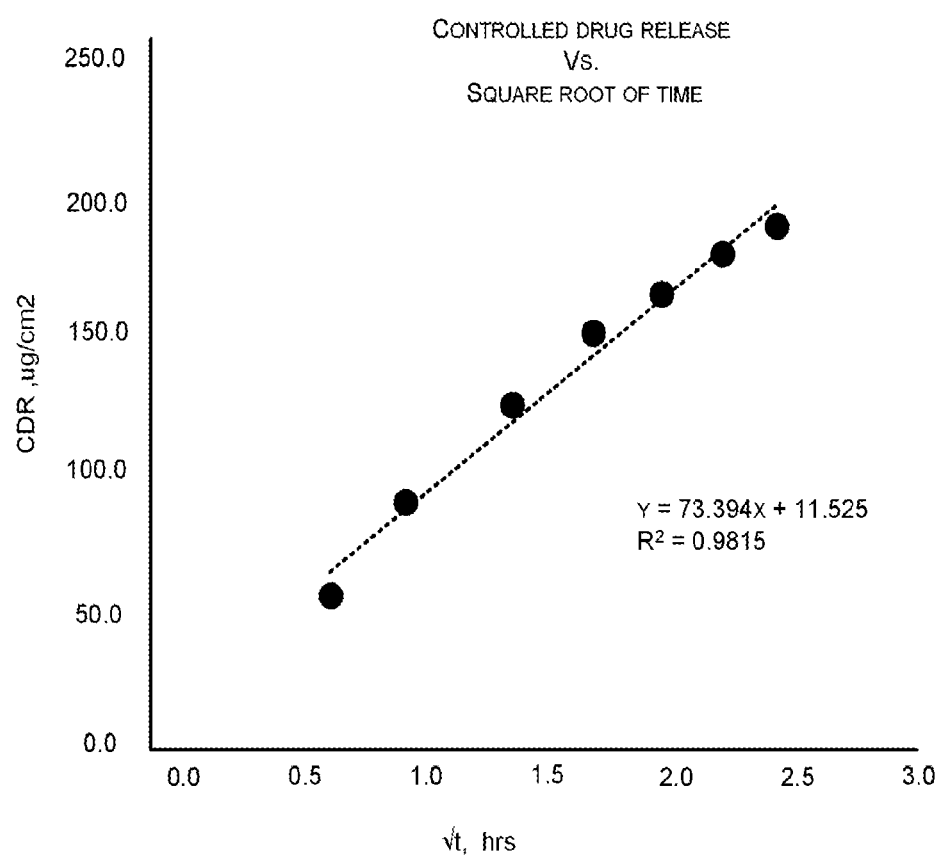
FIG. 3: In-vitro release of Fexofenadine Hydrochloride as a function of $\sqrt{t}$

IVRT study is conducted using different hydrophilic membranes as suggested in FDA guidelines. Below given experimental conditions are maintained for performing the study. PES membrane is selected upon evaluation of different membranes. The results are given in FIG. 3 & Table 30-32 and FIG. 3.

TABLE 29

Experimental conditions

| Apparatus | Vertical Franz diffusion Cell |
|---|---|
| Orifice diameter, mm | 20 |
| Orifice Area, cm$^2$ | 3.14 |
| Cell Volume, mL | 15 |
| Cell temperature | 32° C. |
| Applied Sample weight, g | 0.2 |
| Withdrawn Volume, mL | 0.2 |
| Medium description | pH 2.0, Buffer: Ethanol (60:40) |
| Membrane, size & make | PES, 0.45 µm, 47 mm, Merck Millipore |

TABLE 30

Percentage of fexofenadine release as a function of square root of time

| Time | CDR | √t |
|---|---|---|
| 0.5 | 54.4 | 0.7 |
| 1.0 | 87.1 | 1.0 |
| 2.0 | 121.4 | 1.4 |
| 3.0 | 146.7 | 1.7 |
| 4.0 | 160.2 | 2.0 |
| 5.0 | 174.0 | 2.2 |
| 6.0 | 183.7 | 2.4 |

TABLE 31

Summarized parameters of IVRT

| Batch | Flux (µg/cm2/√h) | Correlation coefficient | Coefficient of variation |
|---|---|---|---|
| ACG001C0140039 | 73.39 ± 3.37 | >0.9 | <5% |

It is observed that the release rates decreased considerably with time, whereas the recovery increased. The data obtained is in close agreement with the Higuchi's square root approximations that describes the initial 30% release from topical formulations under perfect sink conditions as linear. The correlation coefficient was found to be >0.9 upon fitting the data into Higuchi's equation.

Another topical composition comprising fexofenadine, corticosteroid and other excipients. The topical formulation can be prepared by following the same method as described in the earlier process

TABLE 32

Composition comprising fexofenadine and hydrocortisone for topical application

| S. No. | Ingredients | % (w/w) |
|---|---|---|
| 1 | Fexofenadine HCL | 0.5% |
| 2 | hydrocortisone butyrate | 0.1% |
| 3 | Propylene glycol | 10.0% |
| 4 | Benzyl Alcohol | 2.0% |
| 5 | White Petrolatum | 5.0% |
| 6 | Light Mineral oil | 6.0% |
| 7 | Cetostearyl alcohol | 7.0% |
| 8 | Ceteareth 20 | 2.2% |
| 9 | Lemon oil natural | 0.1% |
| 10 | Purified Water | QS to 100% |

TABLE 33

Composition comprising fexofenadine and diphenhydramine HCL for topical application

| S. No. | Ingredients | % (w/w) |
|---|---|---|
| 1 | Fexofenadine HCL | 0.5 |
| 2 | Diphenhydramine HCL | 1.0 |
| 3 | Propylene glycol | 10.0 |
| 4 | Benzyl Alcohol | 2.0 |
| 5 | White Petrolatum | 5.0 |
| 6 | Light Mineral oil | 6.0 |
| 7 | Cetostearyl alcohol 50 | 7.0 |
| 8 | Ceteareth 20 | 2.2 |
| 9 | Purified water | Qs to 100 |

Method of Preparation of Topical Lotion Formulation of Fexofenadine and Diphenhydramine HCL:

Step 1: Charge white petrolatum, fight mineral oil, ceteareth 20 and cetostearyl alcohol into a vessel 1 and heat up to 70° C.-80° C. to dissolve all the excipients.

Step 2: Take propylene glycol and benzyl alcohol in vessel 2 and dissolve fexofenadine HCl completely using magnetic stirrer for 30 minutes.

Step 3: Take 65% in batch quantity of water into a vessel 3 and dissolve diphenhydramine hydrochloride and heat up to 70° C.-80° C.

Step 4: Add warm water in a heating vessel 3 to the water immiscible phase in heating vessel at 70° C.-80° C. and mix to get uniform semi solid phase.

Step 5: Let the temperature of the heating vessel 1, reach to 40° C. slowly then add fexofenadine HCl solution obtained in step 2 to heating vessel 1 and allow to mix completely.

Step 6: Adding lemon oil natural to the semisolid mixture obtained from step 5.

Step 7: Adjust the final weight with water and filled into the container.

TABLE 34

Composition comprising fexofenadine with non-aqueous ingredients

| S. No. | Ingredients | ACG001C-0140053 A % (w/w) | ACG001C-0140053 B % (w/w) | ACG001C-0140053 C % (w/w) |
|---|---|---|---|---|
| 1 | Fexofenadine HCL | 0.5 | 0.5 | 0.5 |
| 2 | Propylene glycol | 10.0 | 10.0 | 10.0 |
| 3 | Benzyl Alcohol | 2.0 | 2.0 | 2.0 |
| 4 | White Petrolatum | 78.0 | 5.0 | 60.0 |
| 5 | Light Mineral oil | 5.0 | 78.0 | 5.0 |
| 6 | Cetostearyl alcohol | 5.0 | 5.0 | 5.0 |
| 7 | Hard Paraffin wax | — | — | 1.5 |
| 8 | Microcrystalline wax | — | — | 7.5 |
| 9 | Lemon Oil | 0.1 | 0.1 | 0.1 |

TABLE 35

Composition comprising fexofenadine with non-aqueous ingredients

| S. No. | Ingredients | ACG001C0140053 D % (w/w) |
|---|---|---|
| 1 | Fexofenadine HCL | 0.5 |
| 2 | Propylene glycol | 10.0 |
| 3 | Benzyl Alcohol | 2.0 |
| 4 | White Petrolatum | 75.8 |
| 5 | Light Mineral oil | 5.0 |
| 6 | Cetostearyl alcohol | 5.0 |
| 7 | Ceteareth 20 | 2.2 |
| 8 | Lemon Oil | 0.1 |

Manufacturing Procedure for Non-Aqueous Composition Comprising Fexofenadine:

Step 1: Charge all the ingredients except drug solution into a heating vessel 1 and heat to 70° C.-80° C. to melt the ingredients.

Step 2: Preparing drug solution: dissolve fexofenadine HCl in propylene glycol and benzyl alcohol in compounding vessel 2 using magnetic stirrer for 30 minutes.

Step 3: Once the temperature of the heating vessel 1, reach 40° C. slowly add drug solution from step 2 and mix completely.

Step 4: Add lemon oil natural to the semisolid obtained from step 3.

TABLE 37

Composition comprising fexofenadine with non-aqueous ingredients ACG001C0140062

| Ingredients | % (w/w) |
|---|---|
| Fexofenadine HCL | 0.5 |
| Propylene glycol | 3.0 |
| Benzyl Alcohol | 2.0 |
| White Petrolatum | 68.5 |
| Light Mineral oil | 20.0 |
| Cetostearyl alcohol 50 | 1.0 |
| Isopropyl myristate | 5.0 |
| Lemon oil natural | 0.1 |

Manufacturing procedure:

Step 1: Charge all ingredients except drug solution into a heating vessel 1 and heat to 70° C.-80° C. to melt the ingredients.

Step 2: Preparing drug solution: dissolve fexofenadine HCl completely in propylene glycol and benzyl Alcohol in compounding vessel 2 using magnetic stirrer for 30 minutes.

Step 3: Once the temperature of the heating vessel 1, reach 40° C. slowly add drug solution obtained from Step 2 to the heating vessel 1 and allow it to mix completely.

Step 4: Optional add Lemon oil natural to the semisolid mix obtained from step 3.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as described above.

I Claim:

1. A pharmaceutical composition comprising:
    H1 antagonist or a salt or a hydrate or a solvate thereof in an amount ranging from 0.001% to 10% w/w;
    a diluent in an amount ranging from 30% to 80% w/w;
    a solvent/co-solvent in an amount ranging from 1% to 30% w/w;
    an emollient in an amount ranging from 10% to 40% w/w;
    a humectant in an amount ranging from 5% to 30% w/w;
    a preservative in an amount ranging from 0.1% to 15% w/w;
    an emulsifier in an amount ranging from 0.1% to 10% w/w; and
    a surfactant in an amount ranging from 2% to 30% w/w, said composition being formulated as a topical formulation.

2. The composition of claim 1, wherein the H1 antagonist is selected from the group consisting of fexofenadine, diphenhydramine, cetirizine, levocetirizine, montelukast and, combinations thereof.

3. The composition of claim 1, wherein the composition comprises an aqueous composition or an non-aqueous composition.

4. The aqueous composition of claim 3, wherein the diluent comprises water.

5. The composition of claim 1, wherein the solvent/co-solvents is selected from the group consisting of ethanol, butylene glycol, propylene glycol, isopropyl alcohol, isoprene glycol, benzyl alcohol, cremophor EL, and combinations thereof.

6. The composition of claim 1, wherein the solvent comprises benzyl alcohol.

7. The composition of claim 1, wherein the preservative is selected from the group consisting of benzyl alcohol, germaben II, propylene glycol, diazolidinyl urea, methylparaben, propylparaben, BKC, Zinc salts, phenoxyethanol, imidazolidinyl urea, sorbic acid, benzoic acid, sodium benzoate, and combinations thereof.

8. The composition of claim 1, wherein the emollient is selected from the group consisting of white petrolatum, light mineral oil, heavy mineral oil, isopropyl myristate, cetyl alcohol, and combinations thereof.

9. The composition of claim 1, wherein the humectant is selected from the group consisting of glycerin, glycerol, propylene glycol, butylene glycol, sorbitol, polyethylene glycol, and combinations thereof.

10. The composition of claim 1, wherein the surfactant, is selected from the group consisting of Polysorbate 20, Polysorbate 40, Polysorbate 60, Polysorbate 80, Span 20, Span 40, Span 60, Span 80, lauramide DEA, TEA, IPM, cocamide DEA, cocamide MEA, glyceryl monostearate, stearic acid, polyethylene glycol ether of cetearyl alcohol, lauroyl polyoxyl-32 glycerides, fatty acid derivatives, and combinations thereof.

11. The composition of claim 1, wherein the emulsifier is selected from the group consisting of cetostearyl alcohol 50, ceteareth 20, polyoxyl cetostearyl ethers, cetyl alcohol, lauroyl polyoxyl-32 glycerides, stearyl alcohol, and combinations thereof.

12. The composition of claim 1, wherein the composition further comprises a skin penetration enhancer in an amount ranging from 0.01% to 10% w/w.

13. The composition of claim 1, wherein the composition further comprises a pharmaceutical agent selected from the group consisting of a corticosteroid, H1 antagonist, a PDE inhibitor, JAK inhibitor, NO releasing drug, an anti-inflammatory agent, an immunosuppressant, an antibiotic, an antifungal agent, a non-steroidal anti-inflammatory agent, a retinoid agent, an antipruritic agent, sun block agent, a keratolytic agent and a combination thereof.

14. The composition of claim 1, wherein the composition is formulated as a solution, spray, lotion, cream, gel, ointment, or as an emulsion, oil in water emulsion, or water in oil emulsion, wherein said emulsion, oil in water emulsion, or water in oil emulsion is for topical administration, dermal administration, or transdermal administration.

15. A composition for topical treatment of an allergic condition comprising: H1 antihistamine or a salt or a hydrate or a solvate thereof, a diluent, a solvent, an emollient, a humectant, a emulsifier, preservative, stabilizer, surfactant and one or more additional excipients; wherein the allergic condition is selected from the group consisting of atopic contact dermatitis, eczema, urticaria, psoriasis, angioedema, hereditary angiodema and combinations thereof.

16. A method of treating an allergic condition, in a patient in need thereof comprising applying to a subject a therapeutically effective amount of the composition of claim 1, wherein the allergic condition is selected from the group consisting of atopic contact dermatitis, eczema, urticaria, psoriasis, angioedema, hereditary angiodema and combinations thereof.

17. The method of claim 16, wherein the composition is formulated as a topical solution, spray, lotion, gel, topical emulsion, cream or ointment.

\* \* \* \* \*